United States Patent
Massey et al.

(10) Patent No.: US 10,701,948 B2
(45) Date of Patent: *Jul. 7, 2020

(54) ANTI-MICROBIAL APPLICATION EQUIPMENT WITH CONTROLS

(71) Applicant: Safe Foods Corporation, North Little Rock, AR (US)

(72) Inventors: Justin Massey, North Little Rock, AR (US); Tim Yeaman, North Little Rock, AR (US)

(73) Assignee: SAFE FOODS CORPORATION, North Little Rock, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/453,402

(22) Filed: Jun. 26, 2019

(65) Prior Publication Data
US 2019/0313657 A1    Oct. 17, 2019

Related U.S. Application Data

(60) Division of application No. 15/349,789, filed on Nov. 11, 2016, now Pat. No. 10,368,556, which is a
(Continued)

(51) Int. Cl.
*A23B 4/30* (2006.01)
*G01F 23/00* (2006.01)
(Continued)

(52) U.S. Cl.
CPC ............... *A23B 4/30* (2013.01); *G01F 23/00* (2013.01); *G01F 23/0015* (2013.01);
(Continued)

(58) Field of Classification Search
CPC .................................. A23B 4/30; G01F 23/00
See application file for complete search history.

(56) References Cited

U.S. PATENT DOCUMENTS 5,133,860 A    7/1992 Tai
5,788,925 A    8/1998 Pai et al.
(Continued)

FOREIGN PATENT DOCUMENTS

WO    WO 2001054502    8/2001
WO    WO 2007084607    7/2007

OTHER PUBLICATIONS

International Search Report and Written Opinion for International Application No. PCT/US2015/048607 dated Dec. 4, 2015. (7 pages).
(Continued)

*Primary Examiner* — Sean E Conley
(74) *Attorney, Agent, or Firm* — Haynes and Boone, LLP

(57) ABSTRACT

A control system for monitoring an antimicrobial application system may include a controller having a monitoring program including an operations unit and an interface unit. The operations unit may include a sensor module operatively coupled to a plurality of sensors positioned to detect operation data associated with the application system in real-time. An adjustment module may adjust the operation of the application system. An analysis module may analyze real-time operation data and initiate a specified response when the analysis indicates that a trigger event has occurred. The response may include issuing a notification to a notification device or initiating the adjustment module to perform a control operation to modify the operation of the antimicrobial application system. A remote monitoring center may control multiple and remote application systems. Mobile devices and a control panel may be operable to interface with operations of the antimicrobial application system via the control system.

9 Claims, 24 Drawing Sheets

Related U.S. Application Data continuation of application No. 15/057,803, filed on Mar. 1, 2016, now Pat. No. 9,491,953, which is a division of application No. 14/846,251, filed on Sep. 4, 2015, now Pat. No. 9,289,001.

(60) Provisional application No. 62/048,024, filed on Sep. 9, 2014.

(51) Int. Cl.
*G05B 15/02* (2006.01)
*G01N 33/00* (2006.01)
*G01V 8/10* (2006.01)

(52) U.S. Cl.
CPC ............... *G01N 33/00* (2013.01); *G01V 8/10* (2013.01); *G05B 15/02* (2013.01); *A23V 2002/00* (2013.01)

(56) References Cited

U.S. PATENT DOCUMENTS

| | | | |
|---|---|---|---|
| 5,980,375 A | 11/1999 | Anderson et al. | |
| 6,455,086 B1 | 9/2002 | Trinh et al. | |
| 6,742,720 B2 | 6/2004 | Nolen | |
| 8,075,857 B2 | 12/2011 | McSherry et al. | |
| 9,491,953 B2 * | 11/2016 | Massey | A23B 4/30 |
| 2003/0047087 A1 | 3/2003 | Phebus et al. | |
| 2004/0052702 A1 | 3/2004 | Shuman | |
| 2005/0153032 A1 | 7/2005 | Hilgren et al. | |
| 2007/0166441 A1 | 7/2007 | Adams et al. | |
| 2009/0196967 A1 | 8/2009 | Nolen et al. | |

OTHER PUBLICATIONS

International Search Report and Written Opinion for International Application No. PCT /US2016/058523 dated Jan. 31, 2017. (18 pages).

\* cited by examiner

| ID | Name | Default Value | Min Value | Max Value | English Caption |
|---|---|---|---|---|---|
| 1 | Language | 1 | 1 | 1 | Language |
| 2 | DipTankFullmA | 8 | 5 | 22 | Full mA |
| 3 | DipTankEmptymA | 4 | 3 | 9 | Empty mA |
| 4 | UseRotary | 0 | 0 | 1 | Use Rotary Filter |
| 5 | SanitationWashCycleDuration | 15 | 10 | 60 | Wash Cycle Duration |
| 6 | SanitationRinseCycleDuration | 15 | 10 | 45 | Rinse Cycle Duration |
| 7 | DipTankRunLevel | 75 | 5 | 99 | Run Level |
| 8 | DipTankCaptureLevel | 99 | 50 | 100 | Capture Level |
| 9 | DipTankPumpProtectLevel | 15 | 3 | 80 | Pump Protect Level |
| 10 | MixingPumpDelayOn | 5 | 0 | 60 | Delay On |
| 11 | MixingPumpDelayOff | 0 | 0 | 20 | Delay Off |
| 12 | MixingPumpRunModeFrequency | 60 | 12 | 80 | Run Mode Frequency |
| 13 | MixingPumpSanitationModeFrequency | 70 | 12 | 80 | Sanitation Mode Freq |
| 14 | MixingPumpAccDecTime | 2 | 1 | 5 | Acc/Dec Time |
| 15 | MixingPumpCaptureFrequency | 50 | 12 | 80 | Capture Frequency |
| 16 | SolutionFillDelayOn | 5 | 1 | 30 | Delay On |
| 17 | SolutionFillDelayOff | 2 | 0 | 10 | Delay Off |
| 18 | SolutionFillPeriodicAddDelay | 60 | 10 | 500 | Solution Add Delay |
| 19 | SolutionFillPeriodicAddDuration | 4 | 1 | 60 | Solution Add Duration |
| 20 | CaptureValveDelayOn | 30 | 2 | 120 | Delay On |
| 21 | CaptureValveDelayOff | 2 | 0 | 10 | Delay Off |
| 22 | CaptureValvePeriodicDelay | 15 | 1 | 60 | Periodic Capture Dly |
| 23 | CaptureValvePeriodicDuration | 10 | 1 | 60 | Periodic Capture Dur |
| 24 | FilterPumpDelayOn | 5 | 1 | 60 | Delay On |
| 25 | FilterPumpDelayOff | 0 | 0 | 10 | Delay Off |
| 26 | FilterPumpRunModeFreq | 60 | 12 | 80 | Run Mode Freq |
| 27 | FilterPumpSanitationModeFreq | 60 | 12 | 80 | Sanitation Mode Freq |
| 28 | FilterPumpAccDecTime | 2 | 1 | 5 | Acc/DecTime |
| 29 | RotaryFilterFreq | 60 | 20 | 80 | Frequency |
| 30 | RotaryFilterAccDecTime | 3 | 2 | 6 | Acc/DecTime |
| 31 | UsePeriodicCapture | 0 | 0 | 1 | Use Periodic Capture |
| 32 | UsePeriodicAdd | 1 | 0 | 1 | Use Periodic Add |
| 33 | DipTankSanitationLevel | 50 | 20 | 95 | Sanitation Level |
| 34 | WaterMeterPulsesPerGal | 30 | 1 | 500 | Pulse/Gal |
| 35 | CecurePumpmLPerStroke | 2 | .1 | 12 | mL/Stroke |
| 36 | DefoamerPumpmLPerStroke | .5 | .1 | 2 | mL/Stroke |
| 37 | UseDosatron | 0 | 0 | 1 | Use Dosatron |
| 38 | UseTankDumpValve | 1 | 0 | 1 | Use Tank Dump Valve |
| 39 | ConcentrationTarget | .4 | .01 | .65 | Concentration Target |
| 40 | PeriodicAddStrokes | 5 | 1 | 100 | Periodic Add Strokes |
| 41 | WaterValveDelayOn | 5 | 5 | 120 | Delay On |

FIG. 14A

| ID | Name | Default Value | Min Value | Max Value | English Caption |
|---|---|---|---|---|---|
| 42 | WaterValveDelayOff | 0 | 0 | 20 | Delay Off |
| 43 | DefoamermLPerGalOfWater | .3 | .1 | .49 | mL/gal of Water |
| 44 | PeriodicAddDelay | 100 | 30 | 500 | Periodic Add Delay |
| 45 | ConcentrationCalibration | 100 | 0 | 170 | Concentration Cal |
| 46 | UseEthernet | 1 | 0 | 1 | Use Ethernet |
| 47 | UseDHCP | 1 | 0 | 1 | Use DHCP |
| 48 | PlantID | 0 | 0 | 9999 | Plant ID |
| 49 | PlantPassword | 1212 | 1111 | 9999 | Plant Password |
| 50 | EngineerPassword | 8989 | 1111 | 9999 | Engineer Password |
| 51 | PhotoEye1PercentThroughput | 50 | 10 | 100 | PE 1 Throughput |
| 52 | PhotoEye2PercentThroughput | 50 | 10 | 100 | PE 2 Throughput |
| 53 | PhotoEye1Min | 80 | 1 | 3000 | PE 1 Min Detection |
| 54 | PhotoEye2Min | 80 | 1 | 3000 | PE 2 Min Detection |
| 55 | PhotoEyeCount | 2 | 1 | 2 | Photo Eye Count |
| 56 | SanitationOverFlowTank | 1 | 0 | 1 | Over Flow Tank |
| 57 | ConveyorUseSpeedControl | 1 | 0 | 1 | Use Speed Control |
| 58 | ConveyorMinFreq | 60 | 20 | 60 | Min Freq |
| 59 | ConveyorMinFreqDwellTime | 10 | 5 | 10 | Min Freq Dwell Time |
| 60 | ConveyorSpanFreq | 60 | 30 | 80 | Span Freq |
| 61 | ConveyorSpanFreqDwellTime | 5 | 1 | 9 | Span Freq Dwell Time |
| 62 | ConveyorRunFreq | 60 | 20 | 80 | Run Freq |
| 63 | FilterTankEmptymA | 4 | 3 | 9 | Empty mA |
| 64 | FilterTankFullmA | 8 | 5 | 22 | Tank Full mA |
| 65 | FilterTankRunLevel | 50 | 20 | 95 | Run Level |
| 66 | FilterTankPumpProtectLevel | 15 | 2 | 80 | Pump Protect Level |
| 67 | SanitationTankDumpDelayOff | 30 | 1 | 160 | Tank Dump Delay Off |
| 68 | SanitationDilutionlevel | 50 | 10 | 99 | Dilution Level |
| 69 | FilterPumpCaptureFrequency | 60 | 12 | 80 | Capture Frequency |
| 70 | UseFlowSensor | 1 | 0 | 1 | Use Flow Sensor |
| 71 | DipTankPipeVolume | 5 | 1 | 30 | Pipe Volume (gal) |
| 72 | PhotoEyeFaultTime | 20 | 10 | 120 | Fault Time |
| 73 | MixingPumpCleanoutInterval | 5 | 1 | 60 | Cleanout Interval |
| 74 | MixingPumpCleanoutDuration | 5 | 0 | 30 | Cleanout Duration |
| 75 | MixingPumpCleanoutFrequency | 60 | 20 | 80 | Cleanout Frequency |
| 76 | UseSolutionTimer | 0 | 0 | 1 | Use Solution Timer |
| 77 | FilterPumpCleanoutFrequency | 60 | 12 | 80 | Cleanout Frequency |
| 78 | PhotoEyeBreakDetectorOnly | 0 | 0 | 1 | Break Detector Only |
| 79 | PhotoEye1BreakDelay | 30 | 10 | 500 | PE 1 Break Delay |
| 80 | SolutionTimerStartDelay | 10 | 1 | 45 | Timer Start Delay |
| 81 | MixingPumpBreakFrequency | 20 | 12 | 80 | Break Frequency |
| 82 | FilterPumpBreakFrequency | 20 | 12 | 80 | Break Frequency |

FIG. 14B

ANTI-MICROBIAL APPLICATION EQUIPMENT WITH CONTROLS

CROSS-REFERENCE TO RELATED APPLICATIONS

This application is a division of Ser. No. 15/349,789, filed Nov. 11, 2016, which is a continuation of Ser. No. 15/057, 803, filed Mar. 1, 2016, now U.S. Pat. No. 9,491,953, which is a division of U.S. patent application Ser. No. 14/846,251, filed Sep. 4, 2015, now U.S. Pat. No. 9,289,001 which claims priority to U.S. Provisional Application No. 62/048, 024, filed Sep. 9, 2014, entitled "Plant Control and Monitoring Apparatuses and Systems," the entire disclosures of which are incorporated herein by reference.

TECHNOLOGY

The present disclosure relates to plant processing equipment for processing foodstuffs and control and monitoring systems and interfaces for the same. More specifically, the present disclosure relates to plant processing equipment and monitoring and control systems for antimicrobial treatment of meat products.

BACKGROUND

Industrial plant operations typically involves an array of interactions between complex processes, equipment, regulations, products, logistics, information technology, personnel, and stakeholders. Traditional methods to address these operations divide the operations into divisions, creating an information gap by complicating the ability of interested parties to obtain cross relevant information. Due to the information gap, important interactions and potential synergies are often overlooked. This may occur even within a single operation system including multiple complex processes.

SUMMARY

In one aspect, an antimicrobial application equipment with controls includes an antimicrobial application equipment comprising one or more components of the group comprising: a rotary screen filter comprising a rotatable, cylindrical body defined by a screen and into which antimicrobial treatment solution is received for filtration of solid components; a plurality of spray nozzles positioned to direct antimicrobial treatment solution onto work pieces as the work pieces are conveyed through a spray cabinet; a dip tank for containing antimicrobial treatment solution and a conveyer for conveying work pieces through the antimicrobial treatment solution contained in the dip tank; a suction box configured to fluidically couple to a dip tank and including a sensor for sensing a level of antimicrobial treatment solution in the dip tank; a capture unit comprising a series of activated carbon filters to filter antimicrobial component from an antimicrobial treatment solution; and a capture unit comprising a series of activated carbon filters each including a header having a plurality of arms defining fluid ports for distributing antimicrobial treatment solution over the activated carbon. The antimicrobial application equipment with controls may further comprise a controller configured to execute a monitoring program. The controller may include an operations unit and an interface unit for interfacing users with the controller. The operations unit may comprise a sensor module operatively coupled to a plurality of sensors positioned to detect real-time operation data associated with operation of the antimicrobial application equipment; an adjustment module operatively coupled to the antimicrobial application unit and configured to adjust the operation of the antimicrobial application unit; and an analysis module configured to analyze the real-time operation data and initiate a specified response when the analysis indicates that a trigger event has occurred, wherein the response comprises at least one of issuing a notification to one or more notification devices or initiating the adjustment module to perform a control operation to modify the operation of the antimicrobial application equipment.

In another aspect, the present application is directed to a control system for monitoring an antimicrobial application system. The system may comprise a controller comprising a monitoring program including an operations unit and an interface unit. The operations unit may include a sensor module operatively coupled to a plurality of sensors positioned to detect real-time operation data associated with operation of the antimicrobial application system. The operations unit may also include an adjustment module operatively coupled to the antimicrobial application system and configured to adjust the operation of the antimicrobial application system. The operations module may further include an analysis module configured to analyze the real-time operation data and initiate a specified response when the analysis indicates that a trigger event has occurred. The response may be one of issuing a notification to one or more notification devices or initiating the adjustment module to perform a control operation to modify the operation of the antimicrobial application system.

In another aspect, the present application is directed to a control system for monitoring multiple antimicrobial application systems. The system may include a multi-plant controller comprising a multi-plant monitoring program. The multi-plant monitoring program may comprise a multi-plant interface unit configured to receive real-time operation data from a plurality of antimicrobial application systems. The multi-plant monitoring system may further comprise a multi-plant operations unit comprising a multi-plant analysis module configured to analyze the real-time operation data and initiate a specified response when the analysis indicates that a trigger event has occurred. The response may include one of issuing a notification to one or more notification devices or initiating a plant controller associated with one of the plurality of antimicrobial application systems to modify the operation of the antimicrobial application system.

In yet another aspect, the present application is directed to a method of monitoring an antimicrobial application system. The method comprises collecting operation data from a plurality of sensors; analyzing the operation data to determine an operational condition; comparing the operational condition to a set point to identify an administrative state corresponding to the set point; and applying an administrative decision rule to the administrative state and initiating a response specified by the decision rule when the administrative state corresponds to a trigger event.

BRIEF DESCRIPTION OF THE DRAWINGS

FIGS. 14A & 14B illustrate a set point table for use with an antimicrobial application system comprising a dip tank according to various embodiments;

DETAILED DESCRIPTION

Figure 1:
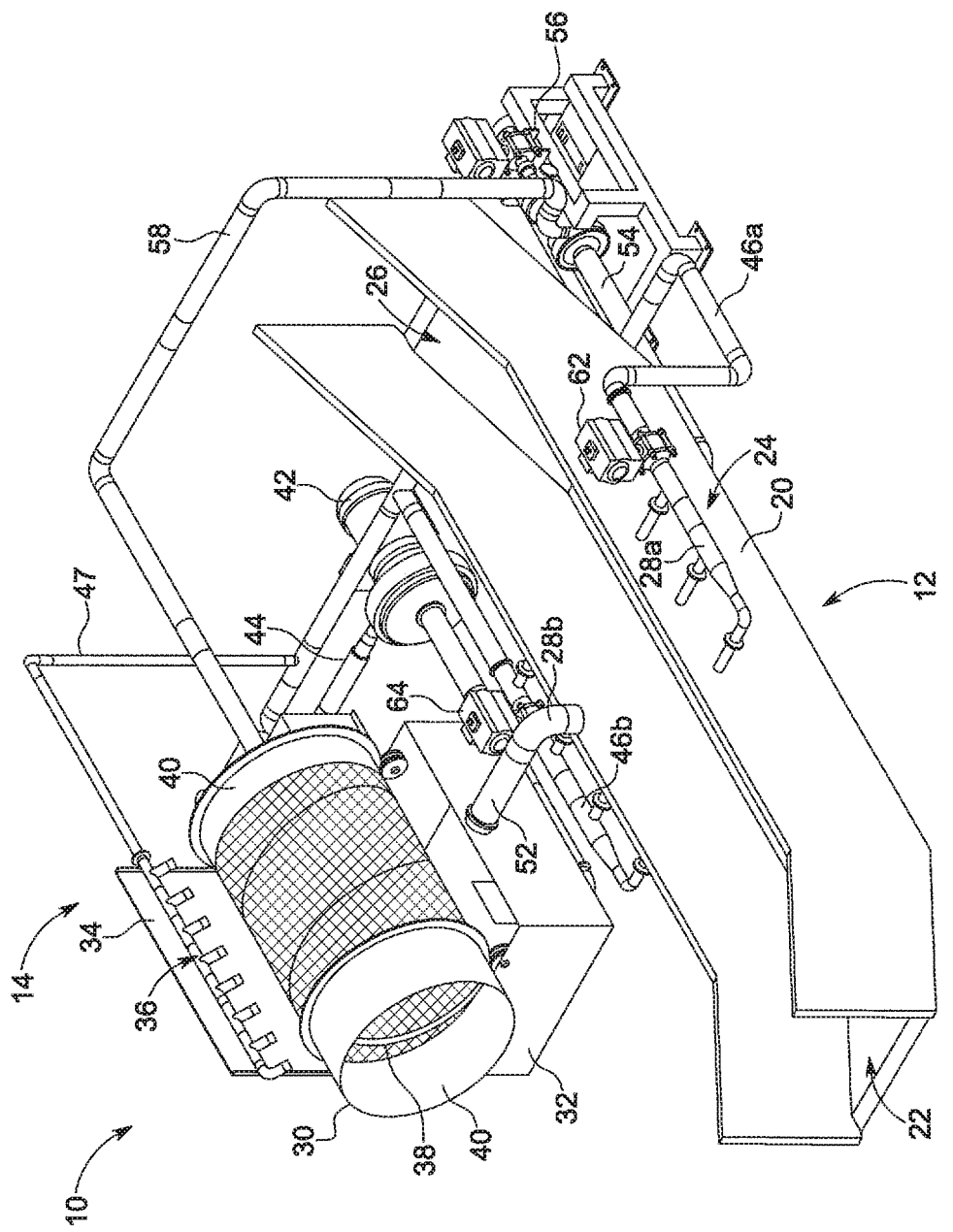
FIG. 1 is a perspective view of an antimicrobial application and recycling system according to various embodiments.
Figure 2:
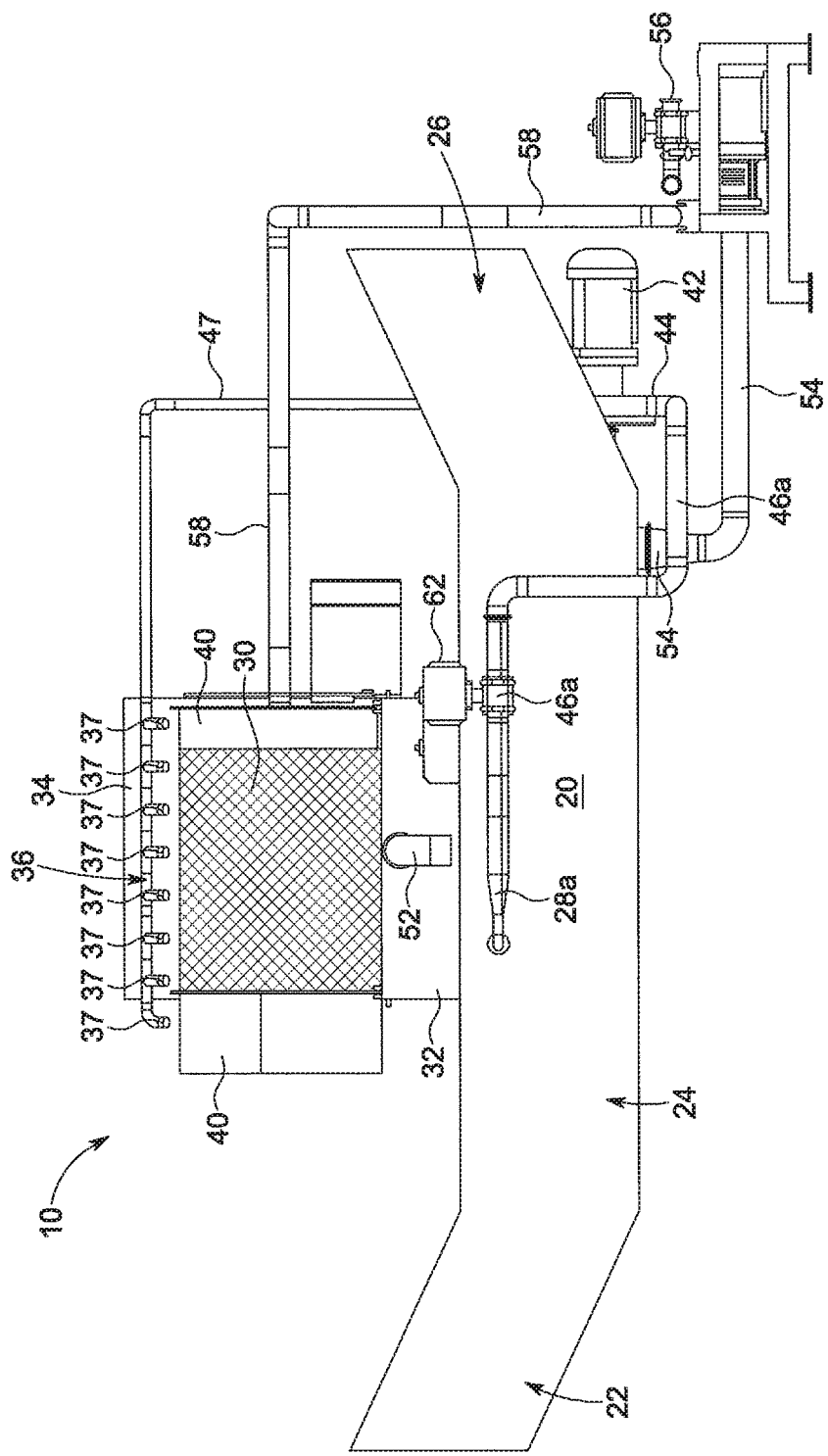
FIG. 2 is a first side view of the system of FIG. 1.
Figure 3:
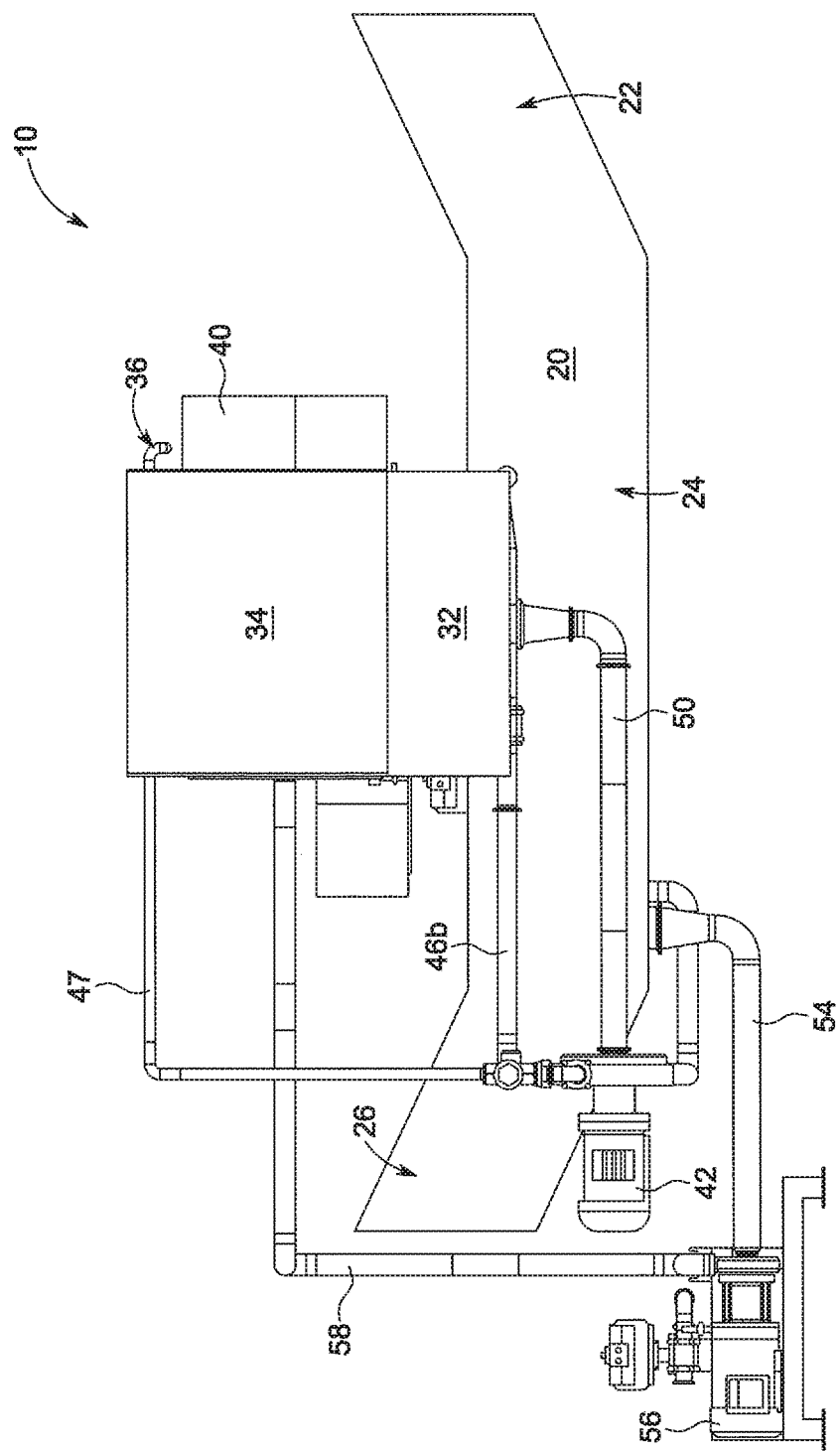
FIG. 3 is a second side view of the system of FIG. 1.
Figure 4:
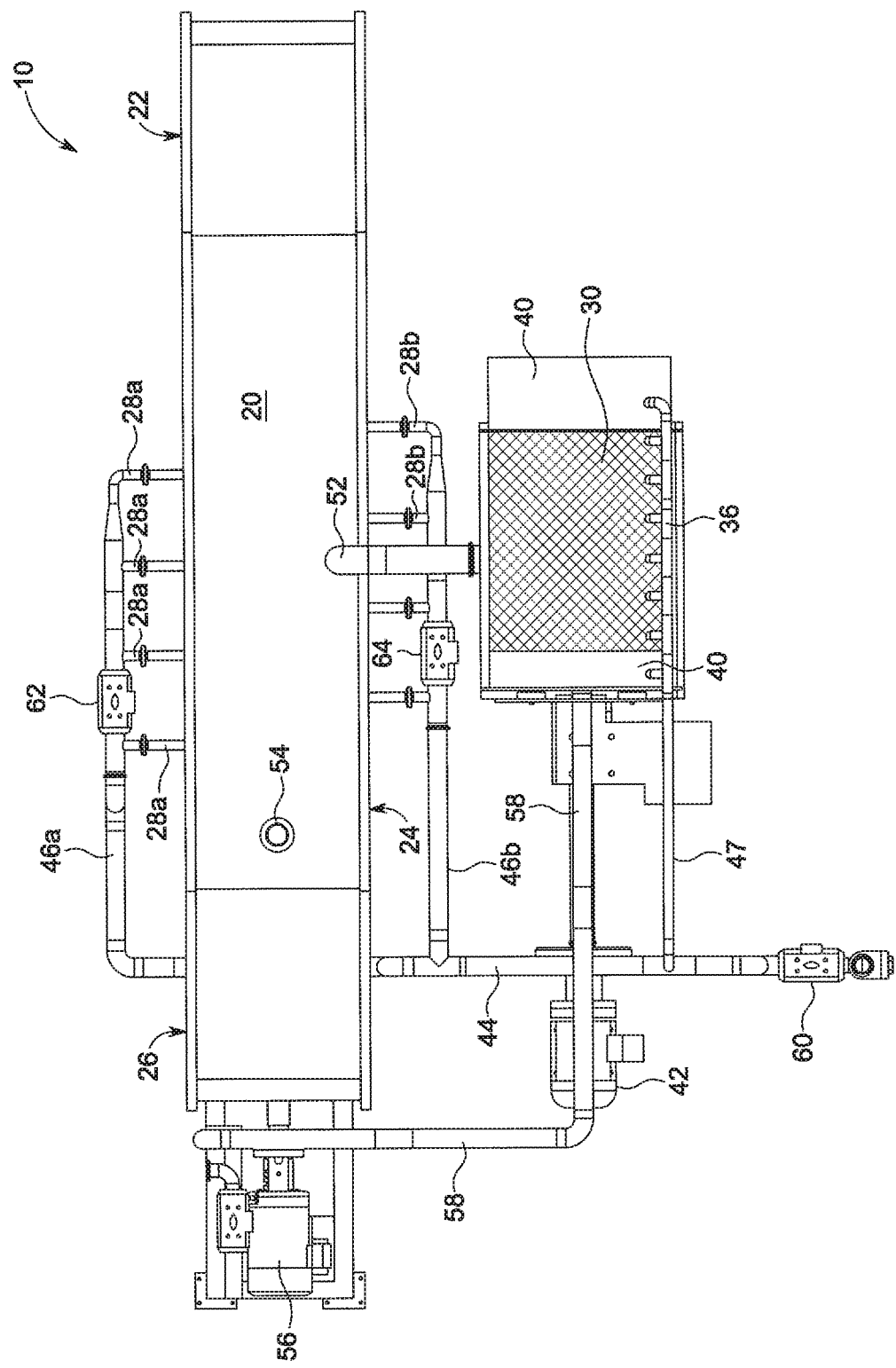
FIG. 4 is a top view of the system of FIG. 1.
Figure 5:
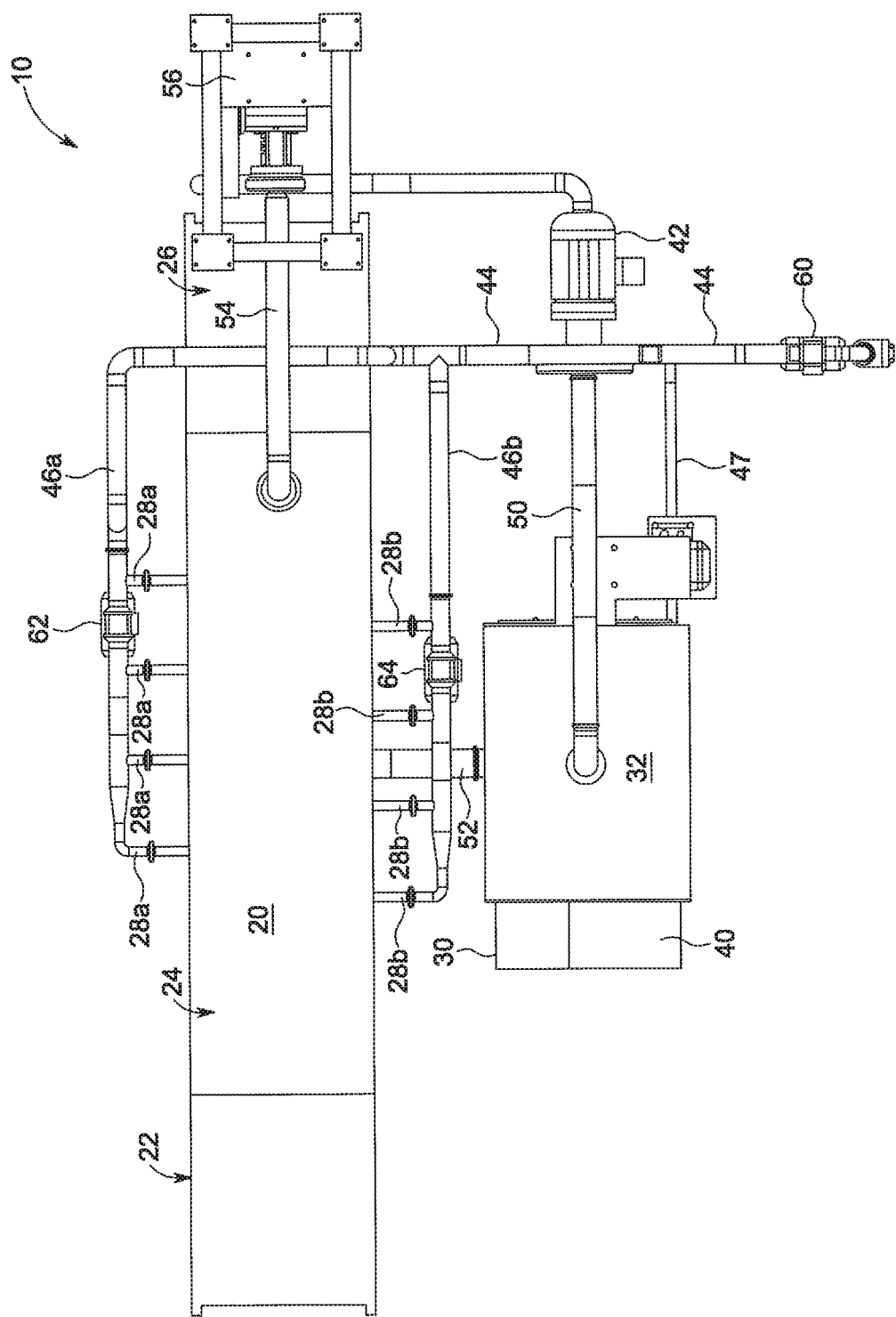
FIG. 5 is a bottom view of the system of FIG. 1.
Figure 6:
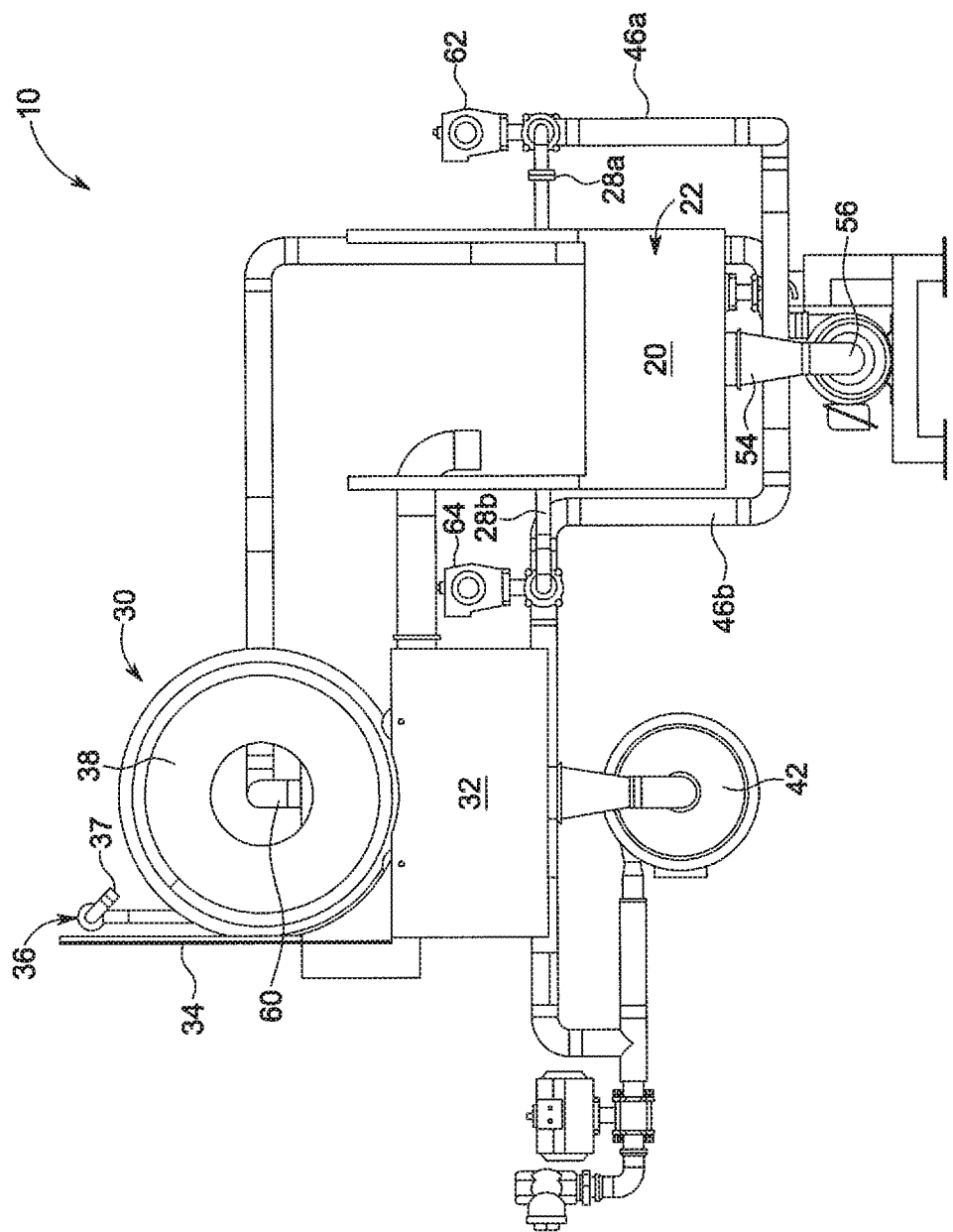
FIG. 6 is an end view of the system of FIG. 1.
Figure 7:
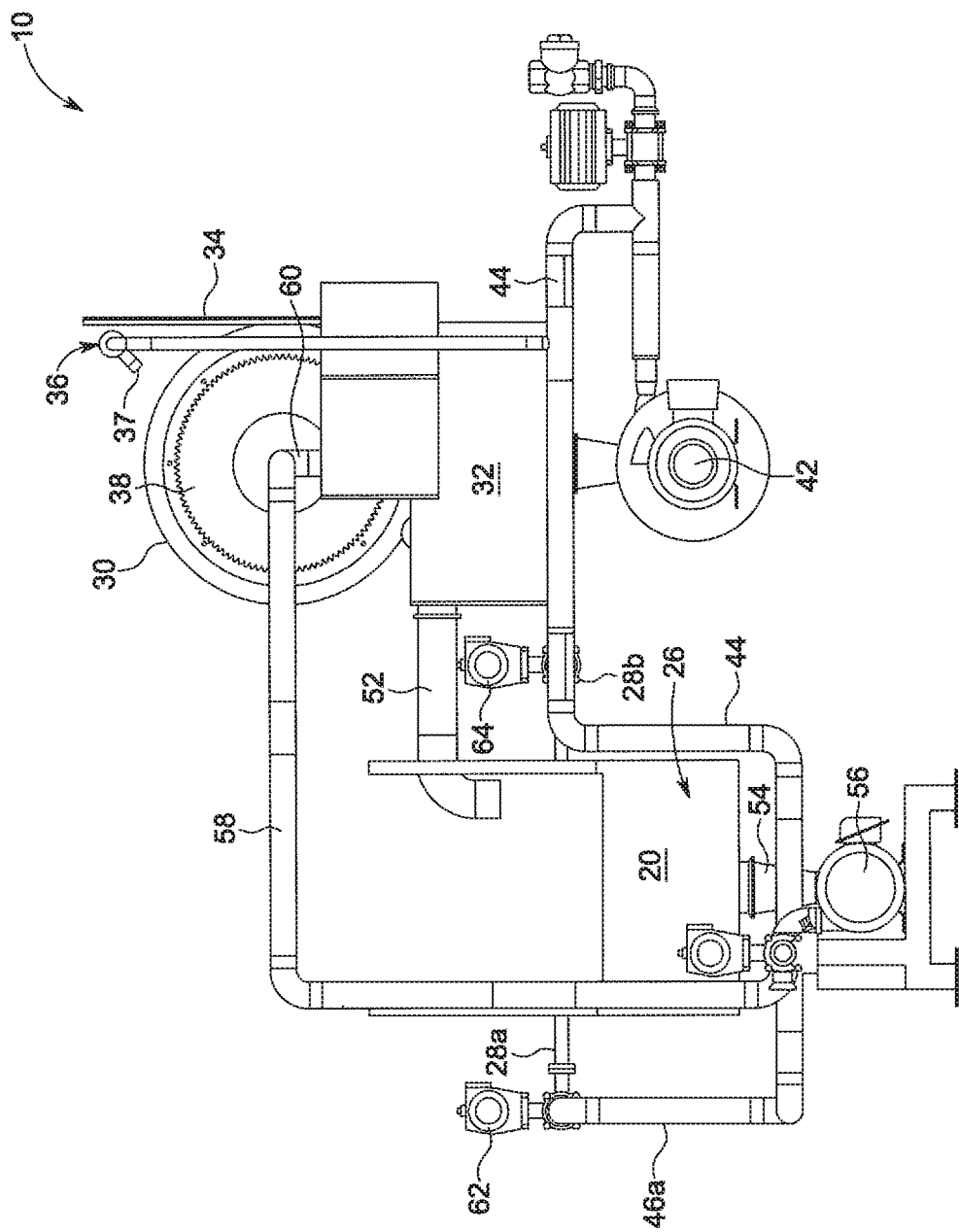
FIG. 7 is another end view of the system of FIG. 1.

In the processing of foodstuffs such as meats, fruits, and vegetables, and particularly in the processing of poultry such as chicken, sanitation of the food product and equipment during processing is extremely important. As herein described, an antimicrobial application system and associated equipment or methods may be employed to apply an antimicrobial solution, e.g., by spraying or dipping the food products to be processed, such as raw meat or chicken parts to reduce microbial contaminants on the meat. As herein described, an antimicrobial application system may be configured to recycle antimicrobial solutions used in connection with food processing. The recycling may include recycling of antimicrobial solution applied to items associated with food processing for subsequent application of the recycled antimicrobial solution to items associated with food processing. The antimicrobial application system may include an antimicrobial application unit and a recycle unit. An initial, dilute antimicrobial composition may be prepared and the concentration of the antimicrobial may be controlled automatically by a control unit. The control unit may include or be operatively controllable by a processor. The processor may be configured to access a data storage medium having stored therein instructions executable by the processor to perform one or more operations of the antimicrobial application system. The antimicrobial composition may be provided to the antimicrobial application unit and applied to work pieces, such as raw poultry carcasses. After application to the work pieces, the antimicrobial composition-containing solution may flow to a recycle tank of the recycle unit. The concentration of the antimicrobial in the antimicrobial solution flowing to the recycle tank may be monitored manually or by the system. Additional antimicrobial may be automatically added if the concentration of the antimicrobial in the antimicrobial solution falls below a desired amount. Additional antimicrobial may also be automatically added at a rate that approximates the rate at which the antimicrobial is depleted from the solution. All or a portion of the antimicrobial solution may be periodically diverted to a capture tank for selective removal of the antimicrobial composition from the solution. The removed antimicrobial and remaining solution are then disposed of in appropriate manners. The antimicrobial is preferably a quaternary ammonium compound, an alkylpyridinium chloride, or cetylpyridinium chloride (CPC). Various different antimicrobial solutions are suitable for use, including, for example, a solution containing cetylpyridinium chloride (CPC). One suitable antimicrobial solution is available under the name Cecure from Safe Foods Corporation.

Referring to FIGS. 1-7, reference numeral 10 refers in general to an arrangement of an antimicrobial application system according to the present disclosure. Although exemplary dimensions are given below for various components of the system, it should be appreciated that the components can be customized for different processing plants, and are therefore not intended to be limiting.

In various embodiments, the antimicrobial application system 10 may be part of a meat processing system employed by a producer or processor of meat. The antimicrobial system 10, for example, may be housed within a larger meat processing plant (not shown) with additional processing apparatuses or devices associated with the meat processing system. The system 10 generally comprises an antimicrobial application unit 12 configured to apply an antimicrobial solution to work pieces, such as raw meat or poultry carcasses or pieces. In some configurations, the antimicrobial application system 10 may further include or be configured to fluidically couple to a recycle unit 14 configured to one or more of receive, supply, retain, transport, mix, deliver, circulate, treat, measure, and filter the antimicrobial solution. For example, in one embodiment, the recycle unit 14 is configured to fluidically couple to the application unit 12 at a first end to receive antimicrobial solution from the application unit 12 and at a second end to deliver antimicrobial solution to the application unit 12. In normal operation of such a configuration, the antimicrobial solution is generally recycled through the recycle unit 14 before passing back to the antimicrobial application unit 12. At the end of an allotted time (for example, a set number of hours, a shift, a day, or longer), processing of the meat products is halted so that the equipment can be cleaned, and the antimicrobial solution is generally then routed through a capture valve 16 for capture in a separation unit (not shown). After capture, the antimicrobial solution may be discarded, or processed for further re-use, depending on the particular application.

Figure 8:
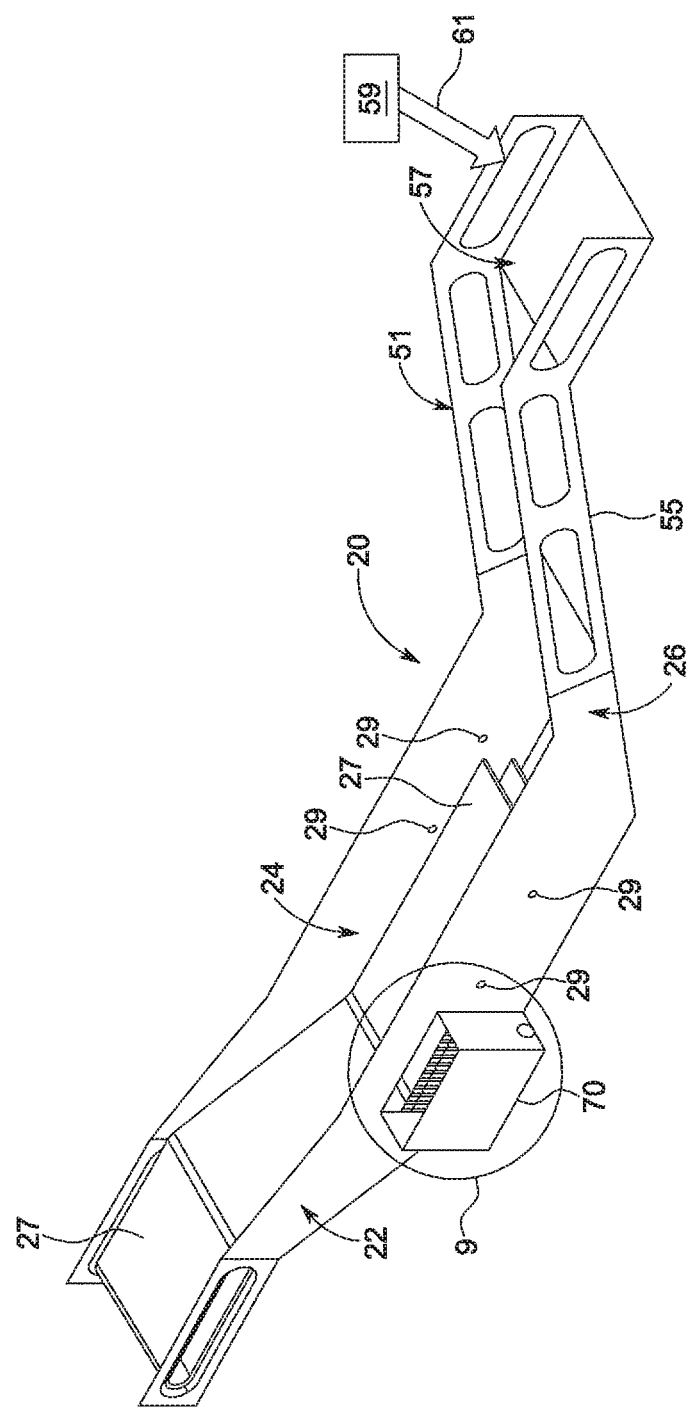
FIG. 8 is a perspective view of an alternative arrangement of dip tank and suction box for use in an antimicrobial application and recycling system according to various embodiments.

The antimicrobial application unit 12 includes a generally trough-like dip tank 20. The dip tank 20 is connected at either end to conveyors for moving parts through the unit 12. The dip tank 20 includes an inlet section 22, a central section 24, and an outlet section 26. A conveyor (not shown) may run along the floor of the dip tank 20. The conveyer may include a moving rack, cage, hanger, or track configured to convey meat products through the dip tank 20. FIGS. 8 and 10 illustrate a conveyer 27 according to various embodiments. The conveyer 27 runs along the dip tank 20 to convey the meat products through the antimicrobial solution 53 within the dip tank 20. The control unit may be configured to maintain a preferred level 53a of antimicrobial solution 53. For clarity, only the portion of the conveyer 27 that extends along the inlet section 22 and through the initial portion of the central section 24 is shown. However, the conveyer 27 will typically extend through the length of the dip tank 20. The conveyer 27 is typically formed of or coated with a noncorrosive material to limit corrosive effects of the antimicrobial solution. The conveyer 27 may include vertical flights to ensure that the meat products are kept continually moving through the dip tank 20. In one embodiment, the conveyer 27 may be a polyethylene belt, and the flights may be 3" tall and spaced every 12" along the belt, although the particular form of the flights will typically be selected in consideration of the product being processed and can vary. These flights may be formed of solid pieces of polyethylene or propylene, for example. The outlet section 26 may include a drip region or drip pan 51 for recycling of excess antimicrobial solution. For example, the drip pan 51 may be positioned downstream of the antimicrobial solution 53 held in the dip tank 20 to catch excess antimicrobial solution from meat products or the conveyer that may be released along the outlet section 26. In one embodiment, the drip pan 51 includes a drain to collect the antimicrobial solution caught in the drip pan 51. The collected antimicrobial solution may then be recycled, e.g., returned to the bulk of the antimicrobial solution held in the drip tank 20. The drip pan 51 may also be positioned at an angle toward the central section 24 to direct the antimicrobial solution caught by the drip pan 51 toward the bulk of the antimicrobial solution 53 held in the dip tank 20. The dip tanks illustrated in FIGS. 1-10 are also equipped with discharge manifolds 28a and 28b provided on each side of the central section 24, and extend through apertures 29 in the sides of the tank 20.

With reference again to FIGS. 1-7, the recycle unit 14 includes a rotary screen filter 30, a rotary screen reservoir 32, a rotary screen shield 34, and a rotary screen spray bar 36. The interior of the rotary screen filter 30 is provided with a screw impeller 38, and each end of the rotary screen includes a solid section 40. The rotary screen filter 30 may be, for example, a 24" diameter stainless steel drum having ¹⁄₁₆ inch perforated holes therein. It will be appreciated that any suitable type and size of screen, such as a mesh or different hole sizes or patterns, may be employed. The screw impeller 38 may take the form of a thread that is about 2" high, and which spirals around the interior of the rotary screen filter 30 to form bands that are about 12" apart.

In various embodiments, the recycle unit 14 includes a rotary screen filter 30 configured to filter solid components from recycled antimicrobial solution. For example, during application of antimicrobial solution to work pieces solids may pass into the antimicrobial solution. The solid components may include, for example, large particles, solids, solids associated with liquids, viscous liquids, fat, gelatinous material, debris, or other materials that may be filtered from the effluent via passage through the size restrictive screen filter 30. One or more additional filters (not shown) may be included in the antimicrobial application system 10, particularly for removing large particles and solids.

The screen filter may include a body including a filter portion 30 positioned between ends 40 of the body. The body may include an annular wall 31 defining a bore that extends along a rotation axis "R" about which the filter portion 30 is configured to rotate as indicated by arrow 33. In various embodiments, the filter portion 30 may be constructed from strips of material patterned or cross-laid to form a plurality of holes or a mesh. The body 30 may also be constructed from a tube or drum through which perforations are formed to define the holes of the mesh 35 between an inwardly facing surface and an outwardly facing surface of the annular wall 31.

The screen filter 30 is preferably coated with or formed of materials resilient to corrosion, e.g., anti-corrosives, stainless steel, synthetics, polymers, plastics, ceramics, etc. The holes of the mesh 35 may be dimensioned to obstruct passage of the solid component having a minimum size or cross-section while allowing passage of the remaining effluent. In one preferred embodiment, the holes of the mesh 35 are sized to define cross-sections of about 0.0625 inches, however, the mesh 35 may include smaller or larger holes as well as fewer or additional holes, e.g., in consideration of the amount, size, or retention characteristics the solid components, rate or quantity of effluent, rotation rate or area of the filter portion, etc. In at least one embodiment, the mesh 35 of the filter portion 30 includes holes having different sized cross-sections.

A primary pump 42 may be configured to pump clean antimicrobial solution around the system. The primary pump 42 is connected to a first distribution conduit 44, from which extend manifold distribution conduits 46a and 46b that are connected to the discharge manifolds 28a and 28b. The distribution conduit 44 can be, for example, a 2" diameter pipe, and a 2" to 1" reducer can be included in the pipe close to the discharge manifolds 28a and 28b. A further distribution conduit 47 is connected between the distribution conduit 44 and the rotary screen spray bar 36.

The discharge manifolds 28a and 28b are located underneath the expected surface of the antimicrobial liquid in the dip tank 20, but above the level of a conveyor belt passing through the dip tank 20. The discharge manifolds 28a and 28b may comprise agitation jets configured to shoot the antimicrobial solution liquid across the reservoir in the dip tank 20, which helps to flip and roll meat products being conveyed therethrough, and therefore unstacks the otherwise stacked product. This allows for an even contacting of all surfaces of the meat product with the antimicrobial solution, which is important to non-oxidative antimicrobial technology such as a CPC-based solution. As CPC has a tendency to foam, submerging the discharge manifolds underneath the expected surface of the liquid in the dip tank 20 helps to reduce foaming.

Underneath the dip tank 20 in the arrangement shown in FIG. 1, a drain conduit 54 is provided. The drain conduit 54 is the primary drain for the dip tank 20, and will receive antimicrobial solution directly after it has been applied to the meat products in the dip tank 20. As this solution will contain organic solids and other particles, the drain conduit 54 may have, for example, an initial diameter of 4" that may pass through a reducer to a 2.5" pipe. Drain conduit 54 is connected to a solids pump 56. A recycle conduit 58 leads from the solids pump 56 to the rotary screen filter 30, and may have, for example, a diameter of 2".

The recycle conduit 58 may include an outlet 60 adjacent to an end 40 of the screen filter 30 that is positioned to deliver effluent into the bore of the screen filter 30. In at least one embodiment, the recycle conduit 58 extends partially within the screen filter 30 and the outlet 60 may include a downspout directed toward or positioned to deliver the effluent to a delivery region that extends along an inwardly facing surface of the annular wall of the screen filter 30. The delivery region may include a band forming one end 40 defining a perimeter of the bore. The band may be formed of the same or a different material as the filter portion 30. The band 40 may have a solid or continuous inwardly facing surface 41 with respect to the bore. The inwardly facing surface 41 may be smooth to discourage accumulation of solid component or from otherwise obstructing flow of effluent from the delivery region toward the filter portion 35. For example, the inwardly facing surface 41 may include a polished metallic surface.

In at least one embodiment, the inwardly facing surface 41 of the band 40 may be textured to include grooves or projections. The grooves may be oriented to provide fluid paths for effluent directed toward the filter portion or to breakup solid components. In one embodiment, the inwardly facing surface 41 may be treated or coated with a non-stick material to discourage accumulation of solid component. In some embodiments, the absence of holes defined in the inwardly facing surface 41 of the band 40 may allow effluent to be delivered into the bore onto the inwardly facing surface 41 while avoiding forcing accompanying solid component onto the filter portion 35 where it may become lodged. The screen filter 30 may include bands 40 positioned at both ends of the body. However, in at least one embodiment, the screen filter 30 includes only one band 40. The screw impeller 38 on the interior of the rotary screen filter 30 helps to move solid particles to the other end 40 of the rotary screen filter, where the particles can fall out of the rotary screen filter into a collection container (not shown) for provision to a further meat processing step, for disposal, or recycling, depending on the application.

In a further embodiment, a lip or ridge may be disposed at an end of the body of the screen filter 30 adjacent to the delivery region to prevent effluent from exiting the bore without passing onto the filter portion 35. In at least one embodiment, however, the inwardly facing surface of the band 40 may be positioned at a raised angle with respect to the horizontal to urge the effluent directed onto the inwardly facing surface 41 of the band 40 toward the filter portion 35 of the screen filter 30. The raised angle may position the inwardly facing surface 41 to oppose the direction of effluent flow with respect to its release from the outlet 60 to redirect the effluent toward the filter portion 35 or may complement the general direction of flow of the effluent toward the filter portion 35. In this or other embodiments, the body 35 of the screen filter 30 may be positioned at an angle with respect to the horizontal such that one end thereof is raised relative to the opposing end. The angle of the body 35 may further angle the inwardly facing surface extending along the filter portion 35. Accordingly, the outlet 60 of the recycle conduit 58 may be positioned to release effluent onto the inwardly facing surface 41 at a high end of the band 40. In these or other embodiments, the outlet 60 may be angled to direct the effluent into the bore or onto the inwardly facing surface 41 of the band 40 at a perpendicular, parallel, or other angle in-between.

As introduced above, the filter portion 35 of the screen filter 30 may be configured to rotate about a rotation axis R as generally identified by arrow 33. In at least one embodiment, the body 35 of the screen filter 30, which may include the band 40, may also be configured to rotate with the filter portion 35. The rotation may be driven by any suitable mechanism configurable to rotate the filter portion 35 of the screen filter 30, such as gears, pulleys, motors, etc.

In at least one embodiment, the screen filter 30 includes a screw impeller 38 configured to urge effluent through the bore. For example, the screw 38 may be configured to urge liquid portions of the effluent along the inwardly facing surface of the annular wall of the screen filter 30, such as the inwardly facing surface 41 of the band 40, toward the filter portion 35. The screw 38 may also be configured to urge solid components along the annular wall through the bore of the screen filter 30 toward a solids trap (not shown). The solids trap may, for example, be located at an end of the body 35 where solid components may be released for disposal. The screw 38 may include a thread protruding from the annular wall toward the rotation axis R. The thread may wrap around the annular wall within the bore between the ends 40 of the body 35 to form a helix therein. The thread may be directionally oriented to complement the rotation of the filter portion 35 to direct separated solid components toward an end 40 of the bore where the solid components may then be passed for disposal. For example, the thread may wrap around the inwardly facing surface in a clockwise or counterclockwise direction with respect to an end 40 of the body 35 to directionally urge solid components toward or away from the end 40 of the body 35 as induced by the direction of rotation and location of the delivery region.

In various embodiments, the screen filter 30 may include or be configured for implementation with a cleaning unit 36. In one form, the cleaning unit 36 may be a spray bar, and may be used to clean one or more portions of the screen filter 30, e.g., dislodge solid components from the annular wall or filter portion 35, provide additional lubrication to encourage passage or solid components through the bore, discourage accumulation of solid components on annular wall or filter portion 35, etc. The cleaning unit 36 may be equipped with a scraper configured to implement cleaning operations of the cleaning unit 36. The scraper may be positioned within or outside the bore. In various embodiments, the scraper may employ various mechanisms to scrape the screen filter 30. For example, the scraper may include one or more extensions such as bristles or rigid or elastomeric flaps, for example, configured to contact the inwardly or outwardly facing surfaces of the annular wall or body 35 of the filter screen 30.

In the illustrated embodiment, the spray bar 36 can have one or more fluid ports 37 configured to direct a fluid onto the annular wall to clean the screen filter 30, e.g., to dislodge solid components from the filter portion 35 or encourage solid components to move along a lower portion of the bore of the filter screen 30 by the action of the screw 38. In at least one embodiment, the spray bar 36 is positioned within the bore to direct fluid onto the inwardly facing surface of the annular wall, e.g., along the filter portion 35 or bands 40. In some embodiments, multiple spray bars 36 or fluid ports 37 may also be positioned around the body 35 or both within the bore and along the outwardly facing surface. The fluid ports 37 may include nozzles configured to directionally enhance or modulate distribution of the cleaning fluid. In certain embodiments, the fluid ports 37 may be statically positioned. Regulation of volume or pressure of cleaning fluid directed from the fluid portions may be modulated using pumps, restriction or obstructive elements, valves, etc. For example, in one embodiment, an orifice plate may be disposed in the spray bar 36. The orifice plate may be positioned to modulate flow for a single or multiple fluid ports 37, for example. In at least one embodiment, the fluid ports 37 may be movable via a central control unit, e.g., in a predetermined or programmed pattern or selectively, which may include sensors configured to sense locations in need of the cleaning action of the fluid and that which send such data to the central control unit for automated directing. In this or another embodiment, the fluid ports 37 may be manually directed via remote controls provided by a user remote control system incorporated with the central control unit.

A distribution conduit 48 is connected to first distribution conduit 44, and provides clean antimicrobial solution to the rotary screen spray bar 36. The distribution conduit 48 may be, for example, a 1" diameter pipe. Antimicrobial solution is filtered through the rotary screen filter 30, and falls on the flow of solid particles being impelled through the rotary filter screen 30, and then out through the bottom of the filter into the rotary screen reservoir 32.

Two outlets are provided in the rotary screen reservoir 32, and are connected to respective conduits. A recycle conduit 50 is connected to an outlet in the bottom of the rotary screen reservoir 32, and is connected in with the first distribution conduit 44 and primary pump 42. An overflow pipe 52 is connected to an outlet at an upper edge of the rotary screen reservoir 32. Overflow pipe 52 is located generally higher than the expected liquid level in the rotary screen reservoir, and may be, for example, a 3" diameter pipe. The overflow pipe 52 can be directed to the top of dip tank 20, and does not need to include a pump as the rotary screen reservoir 32 is positioned above the level of the dip tank 20.

In a normal work shift, the antimicrobial fluid is constantly filtered and recycled in real-time, in a closed loop system, which has a high level of recycling efficiency that retains all of the antimicrobial solution therein. Three capture valves 60, 62, and 64 are provided in the conduit systems so that at the end of a shift, the antimicrobial solution flow can be stopped and can be drained to a capture pipe 66 for capture and further processing. It will be noted that fluid flowing into the capture pipe 66 has been filtered by the rotary screen filter 30 during both the recycle process, and the drain process. This allows the capture line to include a finer grade of filter, such as a carbon filter without having to provide an additional large-scale filter.

Figure 9:
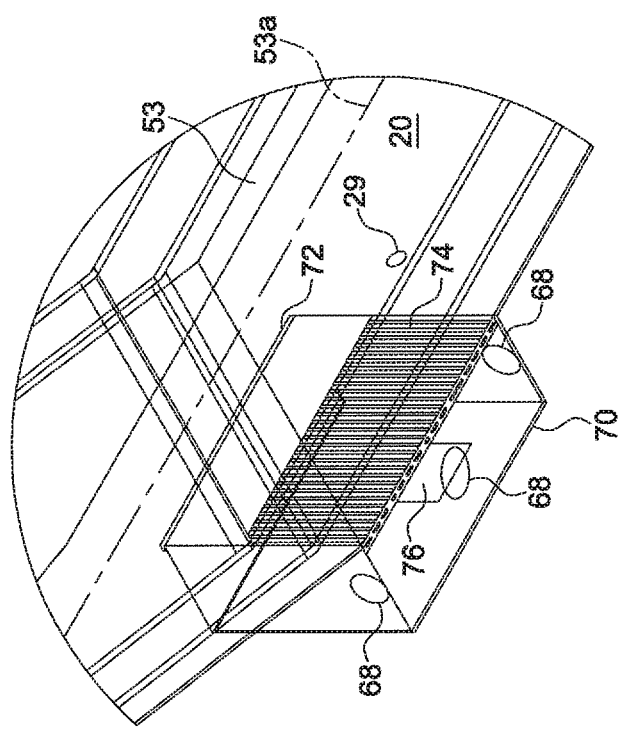
FIG. 9 is a detail view of the suction box of FIG. 8.
Figure 10:
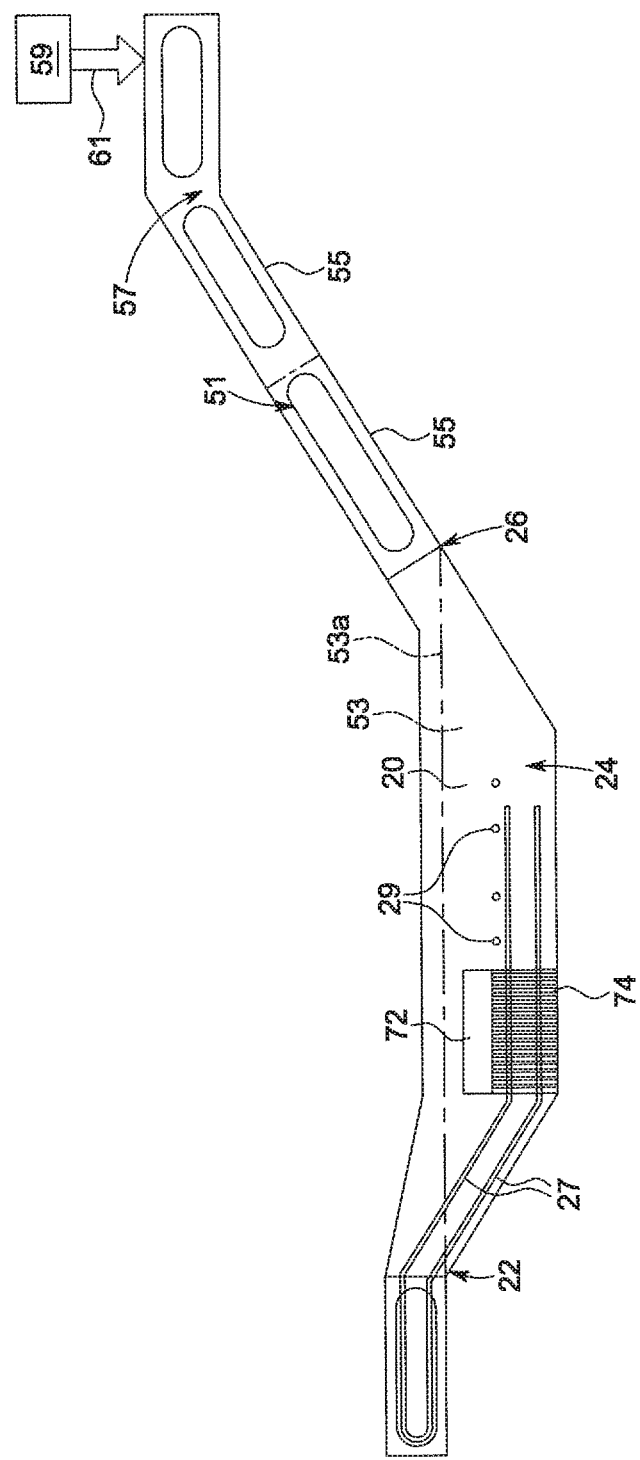
FIG. 10 is a sectional view of the dip tank and suction box of FIG. 8.

Referring now to FIGS. 8-10, an alternative form of drainage from the dip tank 20 is shown. Instead of a drain on the bottom of the dip tank, a suction box 70 is provided to the side of the dip tank 20. The suction box 70 includes a box attached adjacent to an aperture 72 that is cut in the side wall of the dip tank 20. The suction box 70 is separated from the dip tank 20 by a plurality of round bars 74 that act as a screen to prevent the ingress of larger pieces of meat product into the suction box. The bars 74 do not extend all the way to the top of the aperture 72, so that fluid can flow in easily to the suction box, which enables sensors in the box to detect that a sufficient level of liquid is present in the dip tank. For example, a gap of 3-4" may be left between the top of the bars 74 and the top of the aperture 72. This prevents the bars 74 from becoming clogged with smaller meat particulates that may interfere with the operation of sensors 76 in the box, for example, pressure transducers from which the fluid level in the dip tank 20 can be calculated. By placing the sensors in the suction box 70, they can be more easily cleaned or replaced when needed, and by allowing for free flow of fluid into the box 70, the sensors can measure the fluid level in the tank 20 accurately. If needed, the suction box 70 can be briefly separated from the dip tank 20 using a solid plate, so that the sensors may be cleaned while the system is still running, and without stopping the conveyor 27 and bringing the processing system offline in the middle of a shift. Larger meat parts do not clog the suction box bars 74 even with an aperture above the bars, as the larger parts are heavier and remain on the conveyor 27, and are thus prevented from entering the suction box (and hence the recycling conduits) by the bars 74 acting as a filter. One or more drain holes 68 are provided in the base or sides of the suction box 60, to suction away the antimicrobial solution for filtering.

As introduced above, the dip tank 20 illustrated in FIGS. 8 and 10 is configured with an outlet section 26 comprising a drip pan 51. The drip pan 51 may include a downstream length of the outlet section 26 with respect to the central section 24. The drip pan 51 may be integral with the length of the outlet section 26 or may be provided by one or more lengths of modular drip pan extensions 55 that may be coupled to the outlet section 26 to extend the length of the drip pan 51 along the outlet section 26. The drip pan 51 is configured to catch excess antimicrobial solution that associates with the meat products or conveyer after passing through the central section 24. In this embodiment, the drip pan 51 is positioned at an inclined angle away from the central section 24 to direct the excess antimicrobial solution caught by the drip pan 51 back toward the antimicrobial solution 53 within the central section 24 of the dip tank 20. Sensors configured to detect meat products conveyed along the conveyer may be placed along the outlet section 26. For example, in one embodiment, photo eye sensors are positioned adjacent to the conveyer 27 to detect meat products conveyed along the drip pan 51.

The dip tank 20 also includes a stop drip pan 57 downstream of the drip pan 51. The stop drip pan 57 is configured to isolate a rinse solution, which may be applied to the meat products during a rinse application 59, from being recycled with the antimicrobial solution caught by the drip pan 51 or otherwise entering the antimicrobial solution 53. The rinse application 59 may include one or more spray bars having spray nozzles, e.g., vee-jet nozzles for directing the rinse solution 61 onto the meat products after the meat products have been removed from the dip tank 20. The nozzles may be positioned to direct rinse solution 61 to completely cover the width of the conveyer and hence the meat products conveyed on the conveyer 27. The stop drip pan 57 may include a barrier such as a projection or gap positioned between the drip pan 51 and rinse application 59 configured to maintain separation of the rinse solution 61 and the drip pan 51. When a gap is used, rinse solution 61 may be directed toward the stop drip pan 51 which may include a drain for collecting rinse solution 61 following application. In the illustrated embodiment, the stop drip pan 51 includes a length that is horizontal or declined with respect to the drip pan 51 or separated from the of drip pan 51, e.g., includes a gap, to maintain separation of the rinse solution 61 from the antimicrobial solution 53. Accordingly, the stop drip pan 57 may be configured to stop rinse solution 61 from diluting the antimicrobial solution 53.

Administration of a plant operations system in commercial manufacturing or production processes may include a control system configured to integrate various monitoring and control operations into a centralized resource comprising automation, analysis, operational control and monitoring functionalities. For example, the control system may be configured to perform administrative functions with respect to the operation of one or more plant operations systems and associated equipment. The control system may also be configured to integrate one or more of the collection, analysis, storage, access, communication, and distribution of operation data, which may be distributed or made available to specified personnel or devices as defined in the system.

Figure 11:
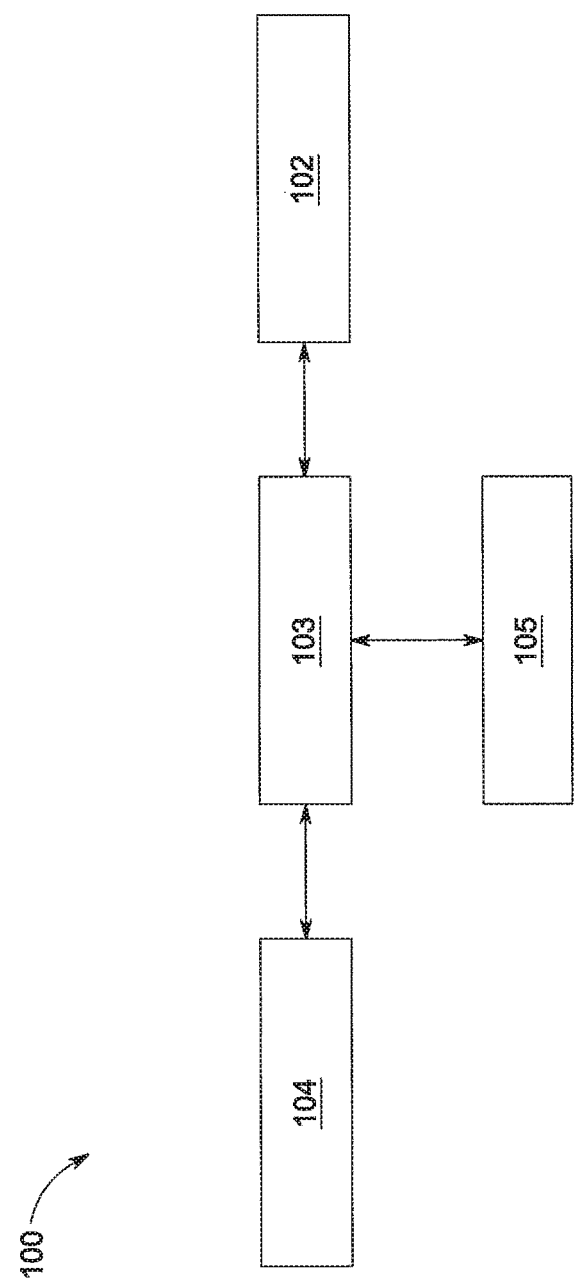
FIG. 11 schematically illustrates an overview of a control system according to various embodiments.

FIG. 11 provides an overview of a control system 100 for administering an operations system 102 according to various embodiments. The control system 100 comprises a flexible platform from which various tasks or functions related to the operations of the plant operations system 102, e.g., controlling or monitoring the anti-microbial equipment of the plant operations system 102, may be configured, defined, controlled, performed, or monitored. The control system 100 may include a controller 103 configured to perform various monitoring and control tasks with respect to the plant operations system 102. In one embodiment, the plant operations system 102 may include a foodstuff antimicrobial application system, which is some applications may include features similar to those described above with respect to the antimicrobial application system 10. In other embodiments, the plant operations system 102 may include an antimicrobial spray applications similar to those described in U.S. Pat. No. 6,742,720, issued Jun. 1, 2004, titled SPRAY APPLICATION SYSTEM, the contents of which are herein incorporated by reference in its entirety. The plant operations system 102 may also include antimicrobial recycling features similar to those described above or antimicrobial capture features, e.g., as described in U.S. patent application Ser. No. 14/510,385, filed Oct. 16, 2014, and titled: ANTIMICROBIAL APPLICATION SYSTEM WITH RECYCLE AND CAPTURE, the contents of which are herein incorporated by reference in its entirety. However, it will be appreciated that the control system 100 may be implemented to provide various control or monitor operations with respect to other operations systems 102 used in various commercial, processing, manufacturing, or industrial applications.

In various embodiments, the controller 103 is configured to operatively associate with one or more sensors (not shown) positioned to sense, detect, or measure conditions of the plant operations system 102 in real-time. The controller 103 may be configured to route or make available operation data to one or more operations database 104 or interfaces 105. The operations database 104, for example, may be accessed by the controller 103 to retrieve, store, or archive control system data, which may include raw, processed, or analyzed operation data, events, as well as parameter definitions, including rules, statistics, tables, algorithms, or other data used to process or analyze data including generating or identifying operational conditions, as described in more detail below. For example, the operations database 104 may include files executable by the controller 103 to perform one or more aspects of the monitoring program 120. The controller 103 may be under the control of the monitoring program 120 configured to interface the functionalities of the controller 103 with users and access devices 142. The monitoring program 120 may define various administrative parameters, e.g., definitions or settings, of the control system 100 such as operational and administrative decision rules including set points, operational condition identification, and analysis parameters, any of which may include customizable definitions to fit a desired application. For example, the controller 103 may be operatively associated with one or more processes of the plant operations system 102 to monitor, collect, analyze, process, and/or communicate data indicative of operational conditions, events, or states as defined by the monitoring program 120.

The controller 103 may also be configured to process the operation data. For example, the controller 103 may analyze the operation data to determine operational conditions, format the operation data into a desired format or generate reports, e.g., enter select data or analyzed data into predefined forms or according to requests received from users via access devices 142. In one embodiment, the controller 103 may be programmed to activate, deactivate, or modulate system pumps or valves, to receive, transmit, or process data signals in communication with one or more components of the plant operations system 102, or to process or analyze data communicated from one or more of the sensors operatively associated with various operation units of the plant operations system 102. For example, the sensors may be configured to detect contaminants or other aspects of antimicrobial fluid composition used for treatment of work pieces. The controller 103 may be operatively associated with one or more data transmission devices which may receive or store data received from or processed by the controller 103. In certain embodiments, the controller 103 may communicate signals to one or more interfaces, e.g., programs, control system or external devices, access devices 142 or applications, or indicators which reflect a condition, event, state, activity, or function of the plant operations system 102. For example, one such indicator may include a notification, which may include activation of a warning light, an audible alert, or a message sent to and displayed on a graphical display associated with a local or remote notification device, plant monitor, or access device.

Analysis of operation data may include the controller 103 utilizing administrative parameters comprising analysis tools to determine, calculate, or classify an operational condition, event, or state and then performing or initiating a predefined response or action in accordance with administrative decision rules specified in the monitoring program 120. For example, the controller 103 may compare raw or processed operation data or an operational condition determined using such data to predefined set points. Set points may include measurable standards identified or specified by a user or otherwise defined in the monitoring program 120. Set points may include, for example, depth or volume of antimicrobial treatment solution within a dip tank of the application unit or recycle unit, discharge manifold or agitation jet pressure applied to jets within the dip tank, conveyer rate, nozzle or line pressure, pump or valve states, antimicrobial concentration, recycle rate, or capture parameters such as rate of capture, effluent composition or flow rate, or expected filter efficiency or remaining life.

When a set point comparison identifies an occurrence of a trigger event, the controller 103 may respond in a predefined way. For example, the controller 103 may transmit to one or more interfaces 105 a notification, alert, or alarm. Additionally or alternatively the controller 103 may perform or initiate a control operation specified by a decision rule, e.g., modulate an operation of the plant operations system 102 to address a trigger event. In various embodiments, set points or the predefined response to a trigger event may be statically or dynamically defined and, thus, may be beneficially configurable to adapt to different operational conditions or circumstances within any given application. In one embodiment, an authorized user may define the statically or dynamically defined response to one or more trigger events.

Figure 12:
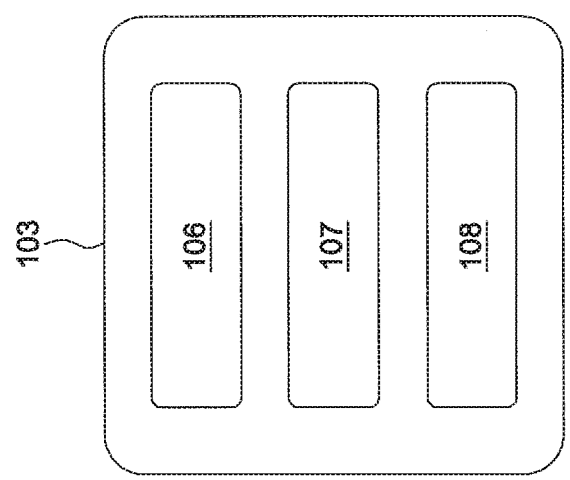
FIG. 12 schematically illustrates hardware units of a controller according to various embodiments.

FIG. 12 illustrates various hardware units of a controller 103 according to various embodiments. In general, the controller 103 may include one or more processors, servers, databases, networks or network devices, and peripherals configured to obtain and transmit data and initiate control operations configured to perform in whole or in part the operations of the monitoring program 120. As shown, the controller 103 comprises a processing unit 106, e.g., one or more electronic data processors or central processing units having logic control functionalities. The controller 103 further comprises a memory unit 107 comprising one or more electronic data storage mediums such as recording media, read-only, volatile, non-volatile, semiconductor based, or other data storage mediums known in the art. The memory unit 107, for example, includes one or more data storage mediums having stored thereon one or more programs or applications comprising software, firmware, or other instructions stored in one or more files executable by the processing unit 106 to perform the various operations and functions of the controller 103. The instructions may include the plant monitoring program 120 or operating system configured to monitor or control plant operations and interface users or access devices 142, which may include interaction with additional applications or services.

The controller 103 may also include a communication unit 108 configured to transmit and receive data. The communication unit 108 may include one or more data ports, communication ports, transmitters, receivers, transceivers, network cards, modems, gateways, routers, switches, firewalls, local, virtual, wide area, cloud/internet area, or internet-based distributed networks, Ethernet, wireless or wired digital communication devices, telecommunication devices, monitors, speakers, lights, buttons, knobs, or peripherals. The controller 103 may also include or be operationally associated with control and monitoring components such as sensors, actuators, valves, pumps, power switches, etc. for controlling or monitoring operational conditions of the plant operations system 102.

The controller 103 may be configured to initiate or otherwise provide control instructions to the plant operations system 102 to modulate plant operations in response to a determination, e.g., to maintain or address deviations in set points. The controller 103 may further be configured to generate event logs, updates, and notifications such as alerts or alarms according to administrative parameters or rules defined by the monitoring program 120 or, in some embodiments, as requested by an authorized user or device. The controller 103 may be configured to transmit operation data to specified access devices 142, users, or the operations database continuously, periodically, in batches, or as otherwise specified in the monitoring program 120, The controller 103 may also be configured to transmit administrative responses in response to trigger events as defined by the monitoring program's 120 administrative decision rules.

Figure 13:
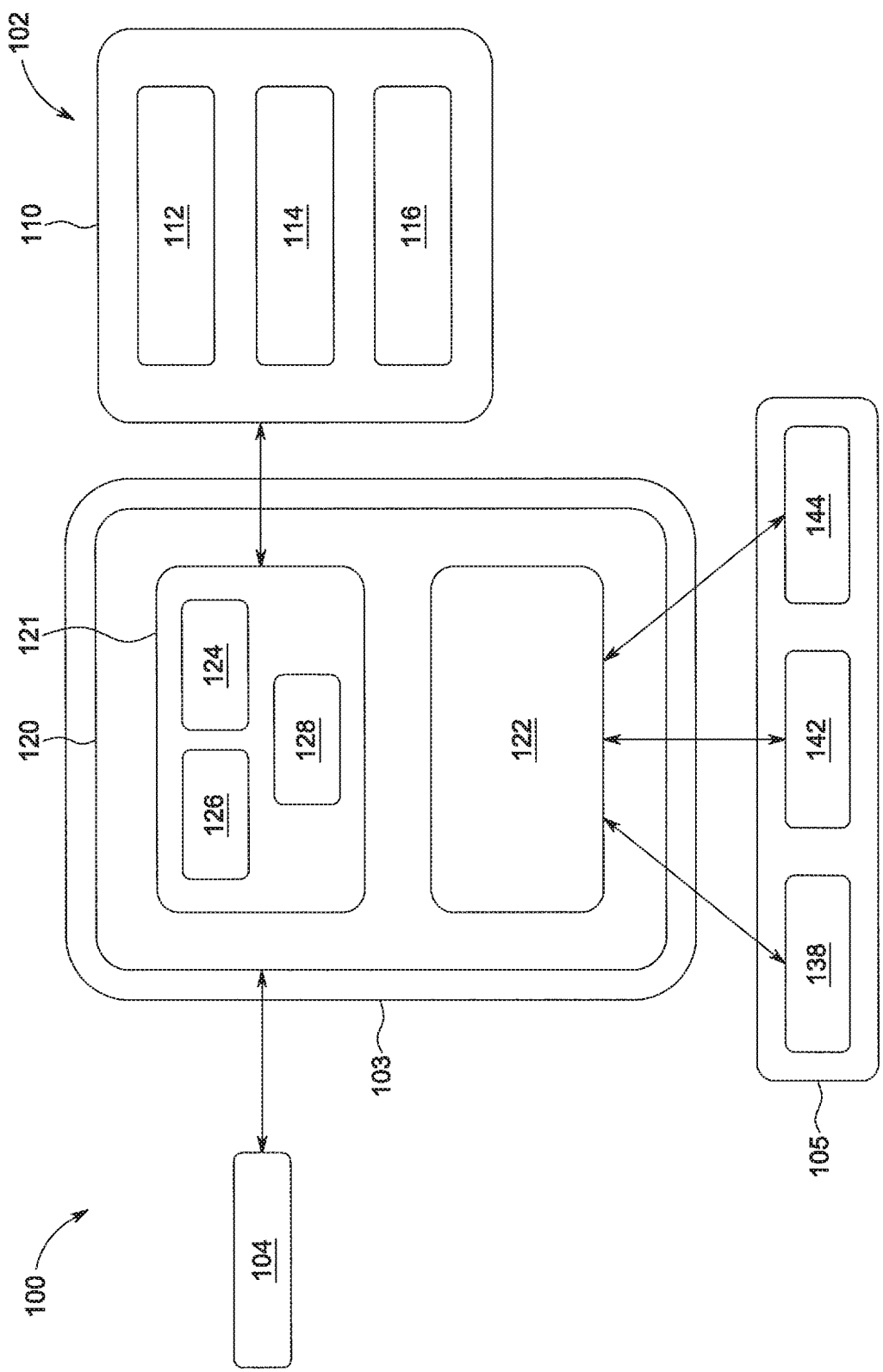
FIG. 13 schematically illustrates features of a control system configured to execute a monitoring program according to various embodiments.

FIG. 13 illustrates one embodiment of the control system 100 according to various embodiments. The control system 100 may comprise one or more networks including networked devices, e.g., nodes or endpoints, configured to communicate via wired or wireless connections. Networks may comprise local, virtual, wide area, cloud/internet area, or internet-based aspects. The networks may include one or more distributed communication networks that may include virtual hardware, distributed databases, parallel or distributed computing schemes, service oriented application architectures, public, private, or hybrid clouds, open architectures or architectures utilizing web API, web applications, or mashups, and may employ client-server or peer-to-peer models.

The plant operations system 102 includes machinery, apparatuses, configurations, and processes by which a plant performs plant operations. For illustrative purposes, the plant operations system 102 depicted in FIG. 13 includes an antimicrobial application system 110, however, the control system 100 may be used to monitor and control other or different operations systems 102. That is, while the control system 100 is described herein in the context of antimicrobial application system 110 for clarity and brevity, it is to be understood that unless specified otherwise the control system 100 may find application in broader contexts such as in manufacturing or other plant processes. The antimicrobial application system 110 may be configured to prepare, circulate, apply, or dispose of antimicrobial treatment solution and transport work pieces for application of the antimicrobial treatment solution. The antimicrobial application system 110 may include various operation units comprising pumps, valves, filters, nozzles, piping, reservoirs, conveying devices, etc., such as those described herein with respect to FIGS. 1-10 and 21-23.

As shown, the antimicrobial application system 110 comprises an application unit 112, a recycling unit 114, and a separation unit 116. The application unit 112 may be configured to apply antimicrobial onto surfaces of work pieces, e.g., raw meat or other food products. The application unit 112 may be similar to the application unit 12 described above and in U.S. patent application Ser. No. 14/510,439, filed Oct. 16, 2014, and titled: CLOSED LOOP RECYCLING SYSTEM AND DIP TANK FOR ANTIMICROBIAL COMPOUNDS, the contents of which are herein incorporated by reference in its entirety. For example, the application unit 112 may include a dip tank containing antimicrobial treatment solution and through which work pieces are transported.

Figure 21:
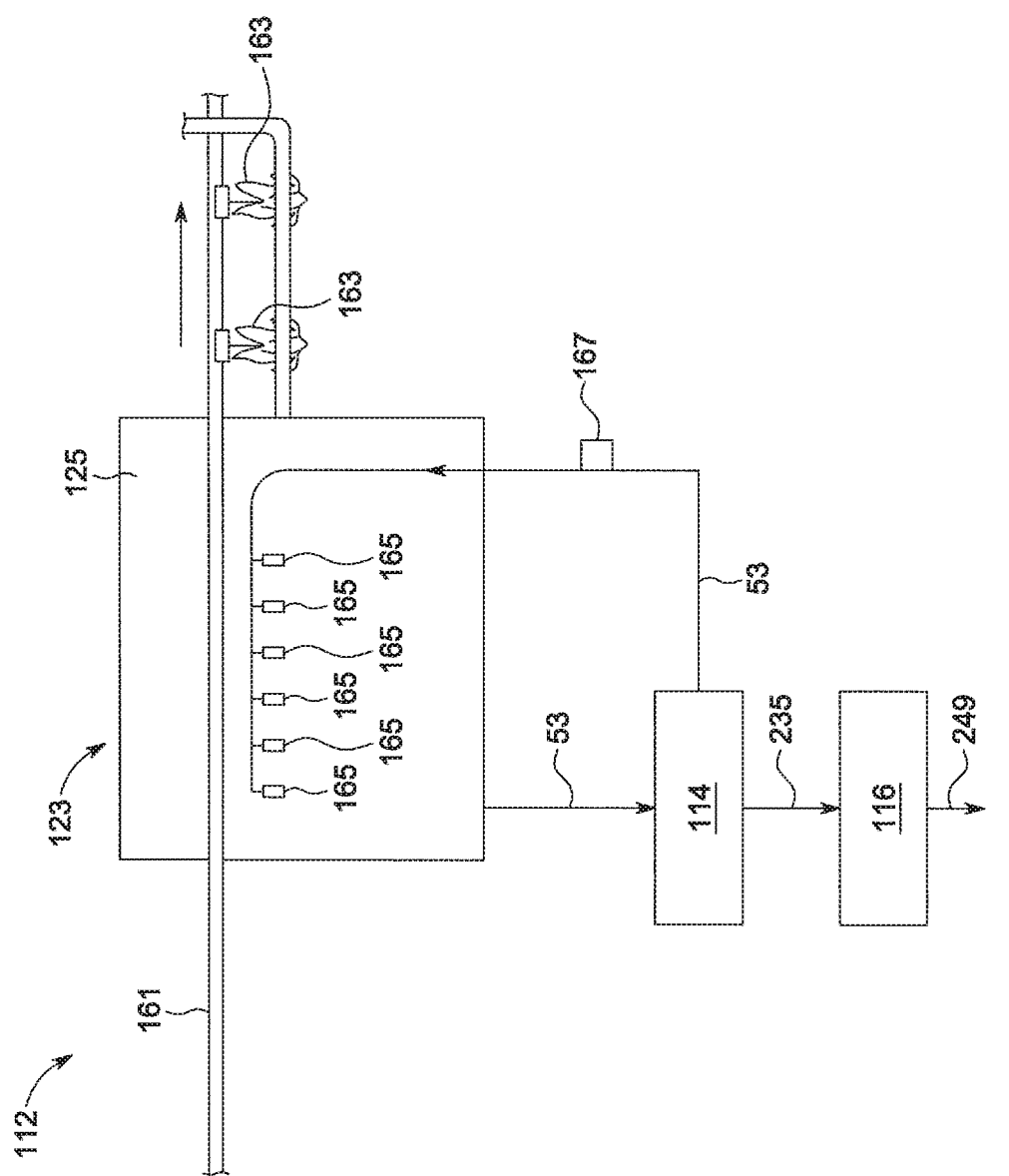
FIG. 21 illustrates an antimicrobial application unit according to various embodiments.
Figure 22:
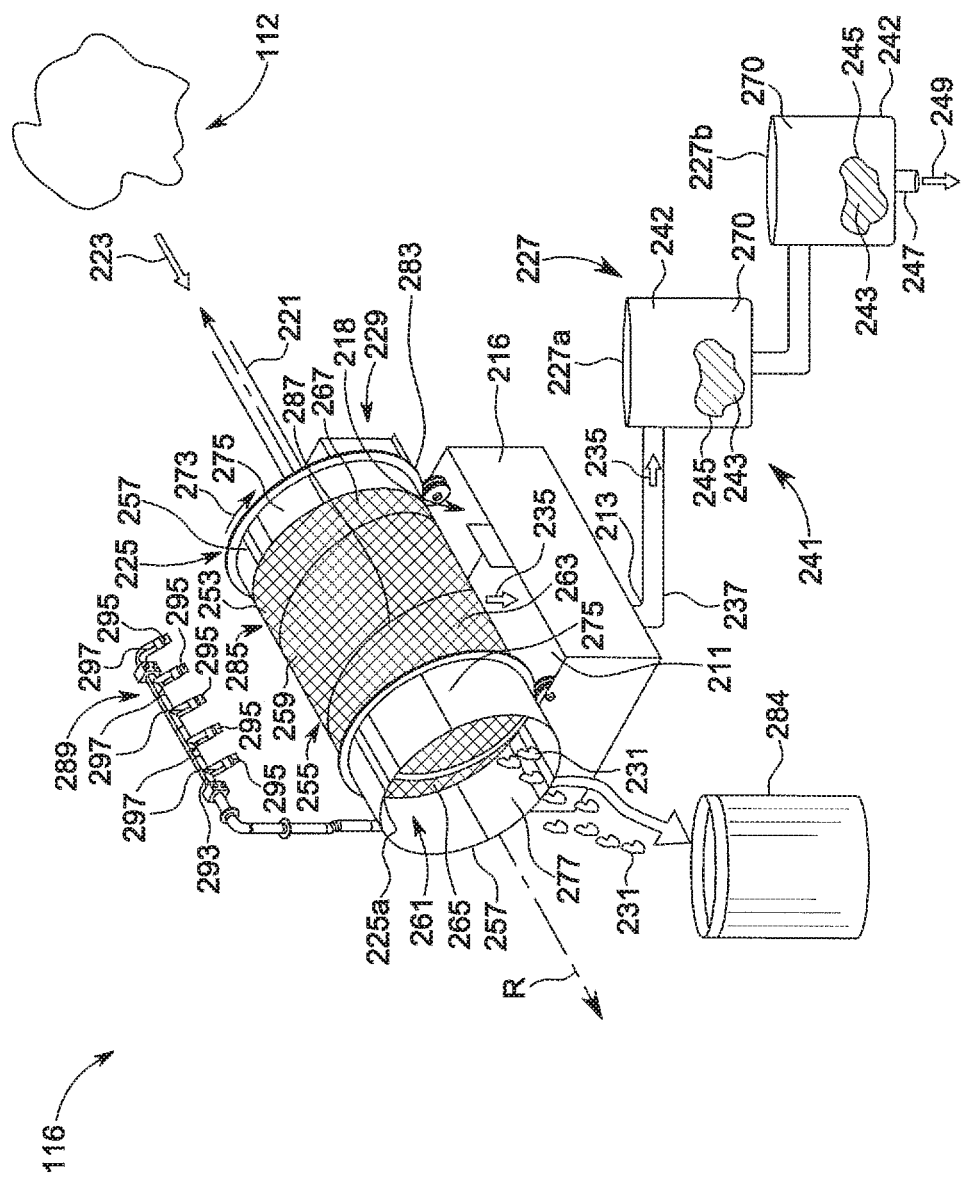
FIG. 22 illustrates a capture unit according to various embodiments.

In another embodiment, the application unit 112 may be configured to apply antimicrobial onto surfaces of work pieces using other or additional manners of application. For example, the application unit 112 may include a cabinet or chamber into which fluid ports or spray nozzles inject or pour a supply antimicrobial treatment solution onto work pieces conveyed thorough the cabinet or chamber. An example of which, is illustrated in FIG. 21. The application unit 112 may comprise a an application unit 123 comprising a cabinet 125. A conveyer 161 extends through the cabinet 125 and is configured to transport work pieces 163 through the cabinet 125. A spray bar comprising a plurality of spray nozzles 165 positioned to direct antimicrobial treatment solution 53 onto the work pieces is positioned adjacent to the cabinet 125. The antimicrobial treatment solution 53 is collected at the cabinet for recycling by the recycle unit 114. A pump may thereafter transport the recycled solution 53 back through the spray bar for additional treatments. An orifice plate 167 may be positioned between the pump and the spray nozzles 165 to maintain a consistent rate of flow from the nozzles 165. At the end of a treatment cycle, for example, antimicrobial effluent 235 may be transported to a capture unit 116 for capture of antimicrobial component and disposal of the filtrate 249. Further examples of application units 112 are described in U.S. Pat. No. 6,742,720, issued Jun. 1, 2004, titled SPRAY APPLICATION SYSTEM and U.S. patent application Ser. No. 14/471,846, filed Aug. 28, 2014, and titled APPLICATION SYSTEM WITH RECYCLE AND RELATED USE OF ANTIMICROBIAL QUATERNARY AMMONIUM COMPOUND, the contents of both are herein incorporated by reference in their entirety. In another embodiment, the application unit 112 may comprise a mobile applicator configured to transit over work pieces and apply antimicrobial to the surfaces of work pieces. Accordingly, the application unit 112 may include conveyers configured to convey work pieces or applicators through the application unit 112 for application of the antimicrobial treatment solution onto the work pieces. The conveyers may include moving surfaces such as tracks, belts, racks, cages, baskets, or hooks, for example, configured to engage and convey work pieces through the application unit 112. The application unit 112 may further include piping systems configured to transport various quantities of the antimicrobial treatment solution or its components through the application unit 112 and may include pumps for transporting the solution or components and valves configured to modify the transport, e.g., to control routing or to regulate pressures within the piping systems.

The recycle unit 114 may be similar to the recycle unit 14 described above and thus may be configured to recycle antimicrobial treatment solution thorough the application unit 112. For example, the recycle unit 114 may include piping, filters, pumps, valves, fluid ports, or the like configured to transport the solution to, from, or through the application unit 112. An example of another recycle unit 114 controllable by the control system 100 is described in U.S. patent application Ser. No. 14/510,385, filed Oct. 16, 2014, and titled ANTIMICROBIAL APPLICATION SYSTEM WITH RECYCLE AND CAPTURE, the contents of which are herein incorporated by reference in its entirety.

The capture unit 116 may be configured to capture an antimicrobial component from the antimicrobial treatment solution. The operations of the separation unit 116 may generally include filtering of antimicrobial treatment solution to separate the antimicrobial component from the solution prior to disposal, for example, at the end of a treatment cycle such as at the end of a shift or a day or other chosen period of time, to purged all or a portion of the antimicrobial treatment solution from the treatment system 110. The purging may include initiation of a capture sequence or transition to a capture mode that coordinates pump and valve operations to thereby direct the antimicrobial treatment solution to the separation unit 116.

The controller 103 may be programmed to sequentially or simultaneously activate or deactivate one or more valves or otherwise operate a valve or valve apparatus in response to a purge signal. In one configuration, during a purge of the antimicrobial application system 110, the controller 103 may coordinate opening or closing of one or more system valves and the powering on or off of one or more system pumps to empty the antimicrobial application system 110 of antimicrobial treatment solution for processing and disposal of the effluent. The purge signal may be transmitted by a user via an access device 142 or by the controller 103 as a predefined administrative response to a trigger event. Such trigger events may be associated with a condition of the antimicrobial treatment solution, an operational condition of one or more units of the system 110, which may be determined from analysis of operation data and determination of operational conditions with reference to one or more set points, the occurrence of a predetermined event (e.g., number of work pieces processed or fixed period of time), or a variety of other operational conditions. In addition to purging or turning over the antimicrobial application system 110, the controller 103 may be configured to coordinate transport of dilute antimicrobial treatment solution to the separation unit 116 for processing and disposal as part of other system operations, which may include a response to a trigger event, for example, to dispose of diluted samples of antimicrobial treatment solution used for performing antimicrobial component concentration measurements, to adjust the volume of antimicrobial treatment solution circulating through the application unit 112 or recycle unit 114, to partially turnover the system fluids to address a low level contamination, or as otherwise desired.

Figure 23:
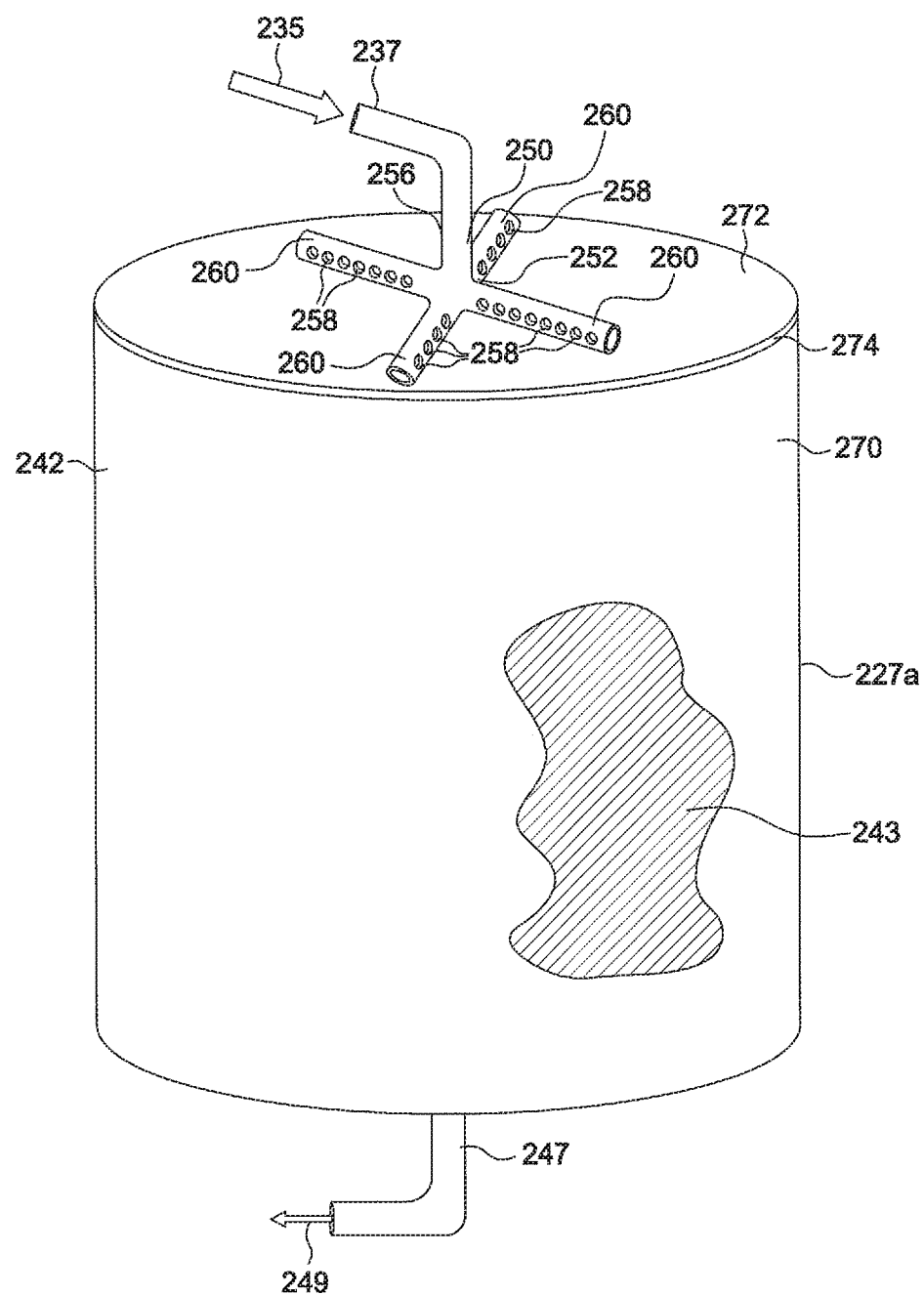
FIG. 23 illustrates a downstream filter of a capture unit according to various embodiments.

FIG. 23 illustrates a capture unit according to various embodiments, the capture unit 116 comprises an upstream filter 225 configured to filter solid component 231, e.g., debris for treated work pieces, of desired size from the effluent 223 and a downstream filter 227 configured to capture antimicrobial component from the effluent 223. The upstream filter 225 may include a screen filter 225a. The screen filter 225a may include a screw 285 configured to urge effluent 223 through the bore 261. For example, the screw 285 may be configured to urge liquid portions of the effluent 223 along the inwardly facing surface 265 of the annular wall 259, such as the inwardly facing surface 277 of the band 275, toward a filter portion 255 comprising a mesh 263. The screw 285 may also be configured to urge solid components 231 along the annular wall 259 through the bore 261 toward a solids trap 284. The solids trap 284 may, for example, be located at an end 257 of the body 253 where solid components 231 may be released for disposal. The screw 285 may include a thread 287 protruding from the annular wall 259 toward the rotation axis R. The thread 287 may wrap around the annular wall 259 within the bore 261 between the ends 257 of the body 253 to form a helix therein. The thread 287 may be directionally oriented to complement the rotation 273 of the filter portion 255 to direct separated solid components 231 toward an end 257 of the bore 261 where the solid components 231 may then be passed for disposal. For example, the thread 287 may wrap around the inwardly facing surface 265 in a clockwise or counterclockwise direction with respect to an end 257 of the body 253 to directionally urge solid components 231 toward or away from the end 257 of the body 253 as induced by the direction of rotation and location of the delivery region 265.

In various embodiments, the screen filter 225a may include or be configured for implementation with a cleaning unit 289. In one form, the cleaning unit 289 may be used to clean one or more portions of the screen filter 225a, e.g., dislodge solid components 231 from the annular wall 259 or filter portion 255, provide additional lubrication to encourage passage or solid components 231 through the bore 261, or discourage accumulation of solid components 231 on annular wall 259 or filter portion 255.

The cleaning unit 289 may be equipped with a scraper 291 configured to implement cleaning operations of the cleaning unit 289. The scraper 291 may be positioned within or outside the bore 261. In various embodiments, the scraper 291 may employ various mechanisms to scrape the screen filter 225a. For example, the scraper 291 may include one or more extensions such as bristles or rigid or elastomeric flaps, for example, configured to contact the inwardly or outwardly facing surfaces 265, 267 of the annular wall 259 or body 253. In the illustrated embodiment, the scraper 291 includes a spray bar 293 having one or more fluid ports 295 configured to direct a fluid onto the annular wall 259 to clean the screen filter 225a, e.g., to dislodge solid components from the filter portion 255 or encourage solid components 231 to move along a lower portion of bore 261 by the action of the screw 285. In at least one embodiment, the spray bar 293 is positioned within the bore 261 to direct fluid onto the inwardly facing surface 265 of the annular wall 259, e.g., along the filter portion 255 or bands 275. In some embodiments, multiple spray bars 293 or fluid ports 295 may also be positioned around the body 253 or both within the bore 261 and along the outwardly facing surface 267.

The fluid ports 295 may include nozzles 297 configured to directionally enhance or modulate distribution of the cleaning fluid. In certain embodiments, the fluid ports 295 may be statically positioned. Regulation of volume or pressure of cleaning fluid directed from the fluid portions may be modulated using pumps, restriction or obstructive elements, valves, etc. For example, in one embodiment, an orifice plate may be disposed in the spray bar 293. The orifice plate may be positioned to modulate flow for a single or multiple fluid ports 258, for example.

In at least one embodiment, the fluid ports 295 may be movable via the controller 103, e.g., in a predetermined or programmed pattern according to the monitoring program 140 or selectively, as directed by a user interfacing with the controller 140 using an access device 142 (which may be a mobile or remote access device or the control panel 138) which may include sensors operatively coupled to the sensor module 124 configured to sense locations in need of the cleaning action of the fluid and that which send such data to the controller 103 for automated or manual directing. In this or another embodiment, the fluid ports 295 may be manually directed via remote controls provided by a user remote control system incorporated with the controller 103, e.g., the interface unit 122 may be configured to provide a remote interface accessible by interfacing an access device 142 or control panel 138 with the monitoring program 140 and transmitting control operations, settings, or other instructions therefrom.

The capture unit 116 may further include a capture tank 216. The capture tank 216 may be positioned along the downstream capture line 237 between the upstream and downstream filters 225, 227 and may include a reservoir 218 for retaining effluent 223. The capture tank 216 may include an inlet 211 to receive the upstream effluent filtrate 235 from the upstream filter 225. The upstream filter 225 may direct or the inlet 211 of the capture tank 216 may be positioned to receive the upstream effluent filtrate 235 directly from the upstream filter 225. For example, the inlet 211 or reservoir 218 may be positioned adjacent to and downstream of the filter portion 255. In some embodiments, additional capture tanks 216 may be included, e.g., the screen filter 225a may include a capture tank 216 positioned to catch upstream effluent filtrate 235 passed through the filter portion 255 which may subsequently be passed to the downstream capture line 237, which may include an additional capture tank 216. In at least one embodiment, the capture tank 216 is disposed between a first portion of the downstream capture line 237a and a second portion of the downstream capture line 237b.

The capture tank 216 may also include an outlet 213 through which effluent 223 may be passed downstream to the downstream filter 227. The outlet 213 may be coupled to the downstream capture line 237 and include a drain or valve configured to open the outlet to allow the effluent 223 to pass from the capture tank 216 into the downstream capture line 237 toward the downstream filter 227. For example, the valve may be configured for manual actuation or automated actuation based on a time, volume of upstream effluent filtrate 235 in the reservoir 218, or capacity of the downstream filter 227. Automated actuation may be in response to a signal provided by the controller 103 according to the monitoring program 140, e.g., in response to a trigger event or as instructed by a user interfacing with the controller 103 via the monitoring program 140 with the control panel 138 or authorized access device 142, which may be a mobile or remote access device 142 comprising a remote interface, or the valve may be mechanically configured to actuate based on a condition of the system, e.g., an upstream or downstream pressure.

Transport of the effluent 223 from the outlet 213 toward the downstream filter 227 may be promoted, for example, by gravity or a pump disposed in or operatively coupled to the downstream capture line 237. In various embodiments, the capture tank 216 may include a siphon. For example, the siphon may be fluidically coupled to the downstream capture line 237. The siphon may be configured to allow the upstream effluent filtrate 235 to collect in the capture tank 216, until it reaches a desired level, wherein the siphon thereafter empties or relieves a predetermined volume of the upstream effluent filtrate 235 from the capture tank 216 and passes the effluent 223 through the downstream capture line 237 toward the downstream filter 227. By incorporation of the siphon or other mechanism configured to avoid continuous passage or trickle of effluent 223, e.g., wherein the monitoring program 140 is configured to initiate the controller 103 to actuate the valves at various time intervals or upon receiving an actuation signal from the monitoring program 140, e.g., in response to a trigger event or as instructed by user interfacing with the controller 103 with the control panel 138 or remote access device 142, the capture unit 116 may reduce or eliminate incidences of channeling with respect to the downstream filter 227. In at least one embodiment, however, the capture unit 116 does not incorporate a siphon or other mechanism configured to avoid continuous passage of effluent 223. In one such embodiment, the capture unit 116 does not include a capture tank 216, rather the downstream capture line 237 is positioned to collect the upstream effluent filtrate 235 from the screen filter 225a and pass the upstream effluent filtrate 235 directly to the downstream filter 227 for continuous processing of the effluent 223 transported to the capture unit 116. As such, the capture unit 116 may be configured for continuous capture and disposal of effluent 223.

The downstream filter 227 may include an antimicrobial separation unit 241. The antimicrobial separation unit 241 may include one or more filter units 227a, 227b, such as disposable carbon filters for selective removal of the antimicrobial component from the effluent 223, wherein the antimicrobial is preferably a quaternary ammonium compound, an alkylpyridinium chloride, or cetylpyridinium chloride. As described above, the filter units 227a, 227b may be configured to exploit one or more characteristics of the effluent 223 or its components to achieve the desired separation of the antimicrobial component 245 from the effluent 223 using any suitable filter strategy and design. In the illustrated embodiment, the filter units 227a, 227b of the separation unit 241 of the downstream filter 227 include at least two filter units that are aligned in series. Each filter unit 227a, 227b includes a container 242 having an outer surface 270 for housing a filter material 243, such as activated carbon, through which the upstream effluent filtrate 235 may be passed for separation of the antimicrobial microbial component 245, e.g., via reaction or adsorption onto the filter material 243. While two filters units 227a, 227b are shown, additional filters may be used. For example, in one embodiment, the downstream filter 227 includes a separation unit 241 having between two and four filter units 227a, 227b aligned in series, wherein each filter unit 227a, 227b includes a container for retaining a supply of filter material 243 including activated carbon.

The downstream filter 227 may include an outlet configured to be coupled to a disposal line 247 to allow downstream effluent filtrate 249 to exit the separation unit 241. In various embodiments, the separation unit 241 is configured to separate a suitable quantity of antimicrobial component 245 from the upstream effluent filtrate 235 such that the resultant downstream effluent filtrate 249 is characterized as having suitably low levels of contaminants or antimicrobial component 245 such that the downstream effluent filtrate 249 is suitable for disposal as plant wastewater discharge in compliance with current effluent guidelines.

In various embodiments, and in further reference to FIG. 23, the antimicrobial separation unit 241 may include a header 250. The header 250 is preferably configured to distribute effluent 223, such as upstream or an intermediate downstream effluent filtrate 235, 249, evenly with respect to the filter material 243, however, in at least one embodiment, the header 250 may be configured to selectively distribute the effluent 223 to one or more regions of the filter material 243 within the container 242. The header 250 includes a body 252 defining an internal fluid path that extends between an upstream inlet 256 and a plurality of downstream fluid ports 258. The body 252 may include one or more arms 260 into which fluid ports 258 may be formed to distribute the effluent 223. The arms 260 may include various arrangements of fluid ports 258 patterned thereon. In the illustrated embodiment, the header 250 includes four arms 160 and may be constructed from piping, for example, and arranged in a crossing or "X" configuration. In other embodiments, however, the header 250 may include other configurations with fewer or additional arms, which may further include secondary arms.

The fluid ports 258 are aligned along two sides of each arm 260. However, in some embodiments, the fluid ports 258 may be aligned along a single side, circumferentially, or along three or more sides of the arms 260 or as otherwise desired to distribute the effluent 223 of effluent filtrate 235, 249 and reduce channeling. For example, as introduces above, even distribution may be desirable to prevent channeling or to increase surface contact between the effluent 223 and the filter material 243. The number and dimensions of the fluid ports 258 may vary to optimize distribution, for example, in consideration of the characteristics of the fluid, filter material 243, or flow conditions. As such, the fluid ports 258 may be dimensioned to restrict, direct, spray, or focus the fluid exiting the header 250. As shown, each of the arms includes twenty-six fluid ports 258. In at least one embodiment, each of two or more arms 260 includes twenty fluid ports. As shown, the header 250 also includes fluid ports 258 having cross-sections between 0.125 to 0.250 inches. However, as described above, additional dimensions and features could also be used depending on the environment in which the system operates. For example, in one embodiment, the header 250 is configured to be movable to increase dispersion of the effluent 223. For instance, the header 250 may be adapted to rotate or selectively move according to a pre-determined pattern. The rate or degree of movement for example may be related to the amount of effluent 223 passing through the header.

The header 250 may be employed in a carbon filtration system including at least two filter units 227a, 227b, as described above. It is to be appreciated, however, that filter units 227a, 227b do not necessarily include a header 250 or the illustrated header 250. Indeed, in at least one embodiment, filter units 227a, 227b include different headers. Similarly, the filter units 227a, 227b may be configured to retain the same or different filter material 243. In one embodiment, one or both of the filter units 227a, 227b may include the header 250. As described above, the filter units 227a, 227b may include containers 242 configured to retain filter material 243. The container may include an inner surface 272 or liner 274 configured to be positioned adjacent to the filter material 243. The header 250 may be suitably positioned at an upstream portion of the container 242 to receive upstream effluent filtrate 235 or an intermediate downstream effluent filtrate 249, as the case may be, and therein distribute the fluid onto the filter material 243. In the illustrated embodiment, the inlet 256 of the header 250 is configured to couple to the downstream capture line 237 to receive the upstream effluent filtrate 235 within the fluid path 254. The header 250 is positioned over the filter material 243 and is configured to distribute the upstream effluent filtrate 249 onto the filter material 243 positioned within the container 242. In operation, the header 250 may be attached to or be positioned within the container 242, which may include a filter drum for example. Distribution provided by the header 250 may reduce or inhibit channeling through the container 242. For example, the header 250 may distribute or sprinkle received effluent 223 or effluent filtrate 235, 249 over a top surface of the filter material 243 to thereby achieve increased distribution and little to no channeling through the filter material 243.

In various embodiments, the antimicrobial separation unit 241 may include a filter unit 227a, 227b in which the container 242 includes a plastic or plastic lined drum configured to contain a filter material 243 comprising activated carbon. As described above, the filter unit 227a, 227b may be disposable such that the activated carbon may be properly disposed of when spent. In contrast to conventional filter units and containers which are typically formed of metals susceptible to corrosion, during their operational lifetime in a capture unit 116 the plastic drum may be configured to avoid such corrosion that may otherwise lead to the occurrence of leaks.

Further examples of capture units 116 controllable by the control system 100 is described in U.S. patent application Ser. No. 14/510,385, filed Oct. 16, 2014, and titled ANTIMICROBIAL APPLICATION SYSTEM WITH RECYCLE AND CAPTURE, the contents of which are herein incorporated by reference in its entirety.

As introduced above, the control system 100 includes a controller 103 configured to execute a monitoring program 120. The monitoring program 120 may include various units and modules that may be implemented to provide the functionalities of the monitoring program 120 including modifying the operations of the treatment system 110. The monitoring program 120 may include a web application, service, or bundled services in which various interfaces 105 such as access devices 142 and notification devices 144 may interface with the controller 103 and monitoring program 120. In various embodiments, access devices 142 may include a control panel 138. Access devices 142 may also include local or remote access devices 142 with respect to the operations system 102. Thus, access devices 142 include mobile or remote interfaces configured to access the controller 103 and the monitoring program 120 functionalities via the interface unit 122. In at least one embodiment, access devices 142 and notification devices 144 may interact with the controller 103 and monitoring program 120 in a cloud platform environment. For example, the various services or applications may be executed in a cloud environment through interaction of the devices 138, 142, 144 and controller 103. In some embodiments, one or more of the devices 138, 142, 144 may store the applications in a data storage medium for execution with a device processor.

As shown, the monitoring program 120 includes an operations unit 121 and an interface unit 122. The operations unit 121 may include a sensor module 124 configured to collect operation data, an analysis module 126 configured to analyze operation data, and an adjustment module 128 configured to adjust an operation of the plant operations system 102 according to the monitoring program 120, e.g., upon receipt of a control instruction from a user or in response to identification or determination of a trigger event.

The sensor module 124 may be associated with, e.g., comprise or be operatively or communicatively coupled with a plurality of sensors associated with one or more of the units 112, 114, 116. The sensors may be positioned at one or more locations to detect and obtain operation data associated with operational conditions. In various embodiments, the operation data associated with operational conditions may be communicated, e.g., transmitted, relayed or routed to, or otherwise obtained by, the sensor module 124 in real-time. Transmission of the operation data may be by any manner known in the art, e.g., via wired or wireless communication. For example, in one embodiment, sensors may be configured to transmit operation data via a wired or wireless transmitter or transceiver configured to transmit the sensed operation data to the controller 103 for analysis by the sensor module 124. In at least one embodiment, the sensor module 124 is configured to transmit instructions to sensors to control initiation, termination, or modification of sensing activities.

The controller 103 may be configured to receive, transmit, analyze, or process operation data. For example, the controller 103, via the analysis module 126, may be configured to process or analyze operation data obtained by the sensor module 124. The controller 103 may be configured to one or more of obtain, analyze, or transmit operation or other control system data in real-time. For example, the sensor module 124 may be configured to obtain operation data for analysis by the analysis module 126 according to the monitoring program 120. The analysis module 126 may be configured to process or analyze, e.g., measure, count, or quantify operation data as defined in the monitoring program 120. In one embodiment, the analysis module 126 is configured to one or more of filter, compile, compare, transmit, route for storage or reporting the operation data. The analysis module 126, via the controller 103, may be configured to access the operations database 104 or memory unit 107 to obtain control system data such as administrative parameters for processing or analysis of the operations data. For example, the control system data may include historical operation or administrative data, event logs, administrative parameters such as formulas, statistics, algorithms, or rules accessible by the controller 103 to process operation data, e.g., to monitor operational conditions of the application unit 112, recycle unit 114, or separation unit 116. The controller may be configured to perform statistical analysis of operation data and hence operational conditions in real-time. In various embodiments, analysis of operation data may include the analysis module 126 accessing the operations database 104 or memory unit 107 to obtain parameters stored therein for determining or assessing operational conditions or states of the operations system 102 from the operation data. The parameters may include predefined set points, statistics, tables, formulas, algorithms, rules, conditional instructions, event data, historical or empirical data from which operational conditions may be determined and assessed from the operation data.

FIGS. 14A & 14B illustrate an exemplary set point table 130 for use in a control system 100 configured to monitor and control the antimicrobial application system 110 comprising an antimicrobial application unit 112 comprising a dip tank. The first column 131 identifies the set point condition. The second column 132 identifies a default value of the set point. The third and fourth columns 133, 134 identify minimum and maximum values or allowable range or variation for the set point. The fifth column 135 provides a quick caption descriptive of the set point condition or a related notation. The set points may be stored in the operation database 104 or memory unit 107 and be accessible by the analysis module 126. In at least one embodiment, the set points may be stored in a removable storage device that may be coupled with the controller 103 for analysis operations. In various embodiments, the set points may include dynamic set points such that the defined values provided in the table 130 may change when the analysis module 126 identifies one or more specified operational conditions. The control system 100 may include multiple set point tables 130 that may be selected by a user or the analysis module 126 upon the identification of an operational condition, state, or in response to a trigger event. As explained in more detail below, the control system 100 comprises a flexible platform in which users may add, modify, or delete set points or set point values. Decision rules or sets of decision rules may also be associated with particular set points or set point tables. For example, following set point analysis of operational conditions, the analysis module 126 may be programmed to query administrative decision rules for characterization of the associated operational state and to initiate the appropriate response to the trigger event. The administrative decision rules may be defined by the user and may be static or dynamic, e.g., may be conditional or modifiable by identified operational conditions, states, or other analysis by the analysis module 126. In one embodiment, a user may define set points and associate administrative decision rules with trigger events associated with the set point. The administrative decision rules may define control operations to modify or tune equipment or operations, notification conditions, or alarm conditions, for example, in response to particular trigger events.

With reference again to FIG. 13, in various embodiments, when operation data or operational conditions are determined to be outside the range defined by the minimum and maximum values specified by an applicable set point, the analysis module 126 is configured to initiate the defined response. For example, the analysis module 126 may be configured to generate or initiate generation of a notification such as a message or warning signal. Alternatively or additionally, the analysis module 126 may initiate a control operation comprising an adjustment of the plant operations system 102 via the adjustment module 128. The adjustment module 128 may be configured to adjust operations of the plant operations system 102. For example, the controller 103 may include or be operatively associated with operation adjustment devices operable by the adjustment module 126 to modify plant operations, e.g., modulate processing rates, speeds, volumes, concentrations, termination or initiation of processes, etc. In various embodiments, the adjustment module 126 may be operable to activate, deactivate, or modulate plant operations such as by controlling or initiating operation of pumps, valves, conveyers, or other components or functions of the plant operations system 102. In at least one embodiment, the analysis module 126 may be configured to initiate intervention by the adjustment module 128 with respect to the operations of the plant operations system 102 automatically, for example, based on a set point defining the occurrence of one or more trigger events, a predefined schedule, as determined from analysis of operation data, such as real-time operation data, or determination of operational conditions.

The interface unit 122 may be configured for interfacing the monitoring program 120 with interfaces 105, which may include users, access devices 142, notification devices 144, or programs. The interface unit 122, for example, may be configured to interface the monitoring program 120 and its functionalities with a control panel 138, which may be a plant control panel or plant computer. The control panel 138 may be local or remote with respect to the plant operations system 102 and its units 112, 114, 116.

The interface unit 122 may also be configured to interface with local or remote access devices 142. The access devices 142 may be configured for two-way communication with the interface unit 122 and may include dedicated or multipurposed devices, e.g., tablets, laptops, personal computers, smart phones, handheld or mobile electronic communication devices, special purpose diagnostic, programming or system administration or computational devices, servers, databases, or other controllers. Communication between or among the interface unit 122 and the access devices 142 may be wired or wireless and may include transmission over one or more networks.

The interface unit 122 may also be configured for one-way communication with notification devices 144 or, in some instances, two-way communication, such as when it is desirable for the notification device 144 to communicate confirmation or a notification or when an access device 142 also includes a notification device 144. Notification devices 144 may include access devices 142 or other communication devices configured to receive signals comprising notifications from the interface unit 122 and initiate an indicator to notify or alert one or more users to a trigger event. For example, the notification device 144 may include or be configured to initiate an indicator such as an audible or visual alarm, light, text message, telecommunication, email, etc. configured to notify or alert the user. In some embodiments, one or more of the access devices 142 may comprise a mobile device that may communicate with additional access devices 142. For example, an access device 142 may access the monitoring program 120 via the interface unit 122 to access the functionalities of the monitoring, e.g., to define or modify settings of the monitoring program 120 used for monitoring and controlling the antimicrobial application system 110. In some embodiments, the access device 142, assuming properly authorized, may access the monitoring program 120 via the interface unit 122 to utilize the functionalities of the monitoring program 120 and associated system devices to directly instruct a change in an operation of the antimicrobial application system 110, e.g., power on or power off pumps, open or close valves, increase antimicrobial component within the treatment solution, increase transit time or belt speed through the dip tank, etc. In one embodiment, access devices 142 may access the interface unit 122 to communicate with other access devices 142 through the monitoring program 120.

As introduced above, the monitoring program 120 may be configured to transmit operation data, plant or operational conditions, notifications, alters or other data, which may include historical, real-time, or projected data, for example, to the various interfaces 105. The interface unit 122 may also be configured to receive new or updated administrative parameters such as set points or values, algorithms, statistics, administrative decision rules such as alarm conditions, notification definitions or instructions such as updated security definitions.

The interface unit 122 may also be configured to receive monitoring program 120 settings or system updates from users, programs, or applications via access devices 142 or the control panel 138. In one embodiment, the interface unit 122 is configured to proactively send control system data to access devices 142, users, or groups of users. The interface unit 122 may also be configured to receive requests from authorized users or access devices 142 for specified control system data. For example, requests may be for event logs, historical data, analyses of operational conditions, reports with respect to one or more operational conditions over specified operational periods. The interface unit 122 may also receive requests or instructions from users, access devices 142, programs, applications, or services for initiation or termination of various activities of the adjustment module 128 configured to adjust the operation of the plant operations system 102. For example, the interface unit 122 may receive operation control instructions from authorized users to view, modify, update, or override operations or states of the control system 100 or operations system 102, such as the antimicrobial application system 110.

In certain embodiments, the monitoring program 120 may communicate signals to one or more notification devices 144 to provide a notification reflecting an state, activity, or function of the operations system 102. For example, one such notification may be transmitted by the interface unit 122 at the direction of the analysis module 128 in response to a trigger event. The notification may be sent to one or more notification devices 144 to include an alert, warning light, or graphical display. In various embodiments, notifications may include emails, phone calls, text messages or alarms.

Figure 15:
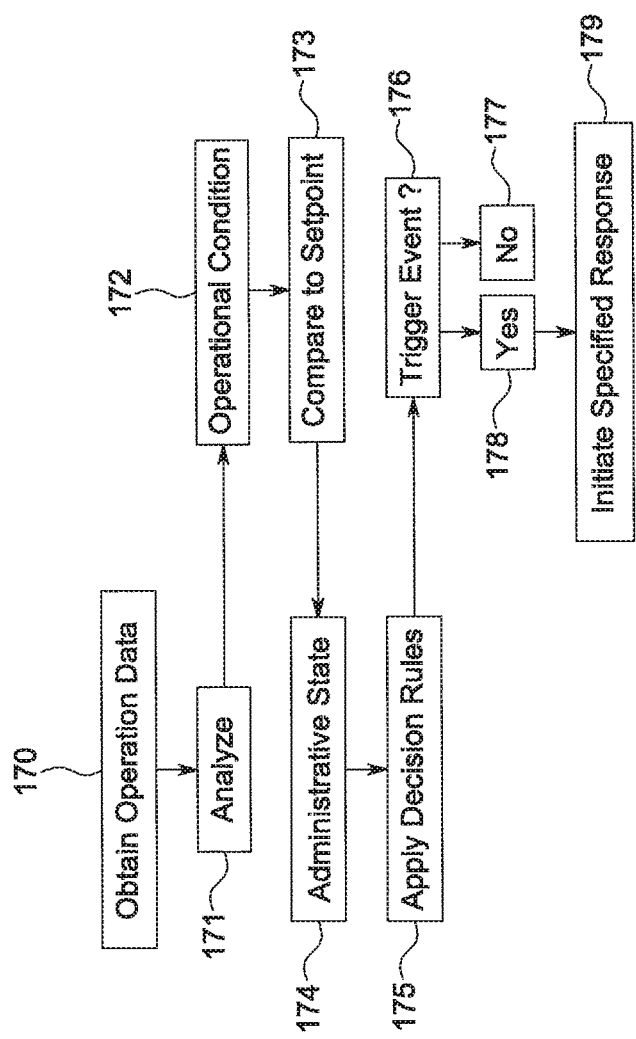
FIG. 15 illustrates an operation of the analysis module according to various embodiments.

FIG. 15 depicts an operation of the monitoring program 120 according to various embodiments. At 170, the sensor module 124 obtains operation data. At 171, the analysis module 126 analyzes the operation data to determine an operational condition 172. The analysis may include analysis of the operation data in a raw form or may include processing the raw operation data as described herein. For example, the analysis module 126 may access and apply administrative parameters, which may include rules, statistics, algorithms, historical data, etc. configured to generate or transform the raw operation data into an operational condition format. At 173, the analysis module 126 compares the operational condition 172 to set points to determine an administrative state 174. At 175, the analysis module 126 queries the administrative decision rules to determine if the administrative state 174 is characterized as a trigger event 176. If the administrative decision rules do not characterize the administrative state 174 as a trigger event 177, the analysis module 126 may take no specific action in response or may apply a default response such as recording or routing the data or analysis to the operations database 104 for archiving or later analysis. If the administrative state 174 is characterized as a trigger event 178, the analysis module identifies the appropriate response 179 specified by the administrative decision rules. For example, application of the administrative decision rules may identify that no action is required in response to the state. The response initiated at 179 may vary depending on the trigger event to be address or as otherwise defined by the user but may include generating or issuing a notification, such as an alarm or message, to a user, access device 142, notification device 144, or specified combination thereof, generating an event log or report identifying the state, time stamping and archiving the state or related operation data, transmitting the state to a multi-plant controller or remote monitoring program or initiating a control operation to modify the operation of one or more aspects of the antimicrobial application system 110 as described herein.

In one embodiment, the sensor module 124 may be configured to obtain operation data related to work piece detection. Work piece detection may include one or more sensors configured to detect work pieces, e.g., optically, by weight, by transit time, etc. For example, in one embodiment, the sensor module 124 may be associated with one or more electronic eyes that may be used in connection with managing concentration of antimicrobial treatment solution. An electronic eye or an array of electronic eyes may be used to detect the presence, number, orientation, or rate, for example, of work pieces processed by the application unit 112. In one instance, the electronic eye or array of electronic eyes is configured to detect work pieces positioned on or suspended from conveyer belts or hooks, such as shackle lines, or submerged in antimicrobial treatment solution. Upon sensing the operation data, the sensor module 124 may provide some or all of the operation data to the analysis module for analysis of one or more operational conditions.

In various embodiments, operational conditions analyzed may be the operation data sensed or measured or may be a condition directly or indirectly derived from the operation data sensed or measured. For example, the number of work pieces in which the antimicrobial treatment solution has been applied may be a variable in an algorithm used by the analysis module 126 to determine an expected concentration of antimicrobial component alone or in combination with other operation data or analyzed operational conditions. For example, configurations of optical sensors comprising electronic eyes may be used by the sensor module 124 to detect work pieces processed or transported along a conveyor belt for processing. The conveyor belt may include a reflector on one side. Work pieces may be detected when obstructing a path or sightline between an electronic eye and a reflector. Upon obtaining or receiving the operation data, the analysis module 124 may be configured to analyze the operation data and take into account the presence of belt features (e.g., flights) that may project outward of the belt surface. For example, the size, number, transit time, or expected location of the belt features may be calculated and filtered from raw operation data. The filtered operation data may then be analyzed for indirect determination of antimicrobial concentration, which in some embodiments may be incorporated into an algorithm applied by the analysis module 126, the set points, or the administrative decision rules. Other operation data may also be useful to determine the concentration of the antimicrobial treatment solution such as the weight the pre and post treated work pieces downstream and upstream of the application area.

In some embodiments, it is desirable to add a food-grade defoaming solution to an antimicrobial treatment solution comprising CFC during the recycling process. Thus, in various embodiments, the analysis module 126 may be configured to initiate the adjustment module 128 to dose the antimicrobial treatment solution with a defoamer. The timing and amount of the dosing may be in response to a trigger event. The administration program 120, for example, may include administrative parameters including an algorithm executable by the controller 103, via the analysis module 126, to direct a periodic add of a defoaming solution to blend into the antimicrobial treatment solution in response to a trigger event. In one embodiment, periodic addition of the defoaming solution may be automated according to the administrative decision rules defined in monitoring program 120 to manage the volume of the defoaming component in the antimicrobial treatment solution in real-time. For example, the analysis module 126 may respond to a trigger event by initiating the adjustment module 128 to add an appropriate dose of defoamer according to a predetermined set of outcomes determined from the analysis of the operation data, which may include comparison of set points and operational conditions identified by the analysis module 126.

The set points may define preparation of antimicrobial treatment solution such that the adjustment module 128 may initiate addition of a volume of water and antimicrobial component to a dip tank or other solution reservoir or line. That is, the adjustment module 128 may perform a control operation comprising a controlled addition of an antifoaming agent to the solution of water and antimicrobial component designed to obtain a target concentration. This may be done based upon a predefined administrative state determined by the analysis module 126 by comparison to one or more predefined set points. The target concentration may be, for example, 0.8% or 0.6% antifoaming agent by weight. The initial concentration may be determined according to the default set point value 132. During operation, the concentration may deviate from the default value 132 and thus this operational condition must be monitored by the operations unit 121. When operation data or analysis of operation data determines operational conditions are such that the concentration of defoamer or antimicrobial component is outside the minimum/maximum 133/134 range, the analysis module 126 may initiate addition of defoamer or antimicrobial component. As described above, the determination may be based in part on the number of work pieces treated and thus may incorporate historical operation data, statistics, or algorithms in conjunction with real-time data to indirectly determine solution composition.

Figure 16:
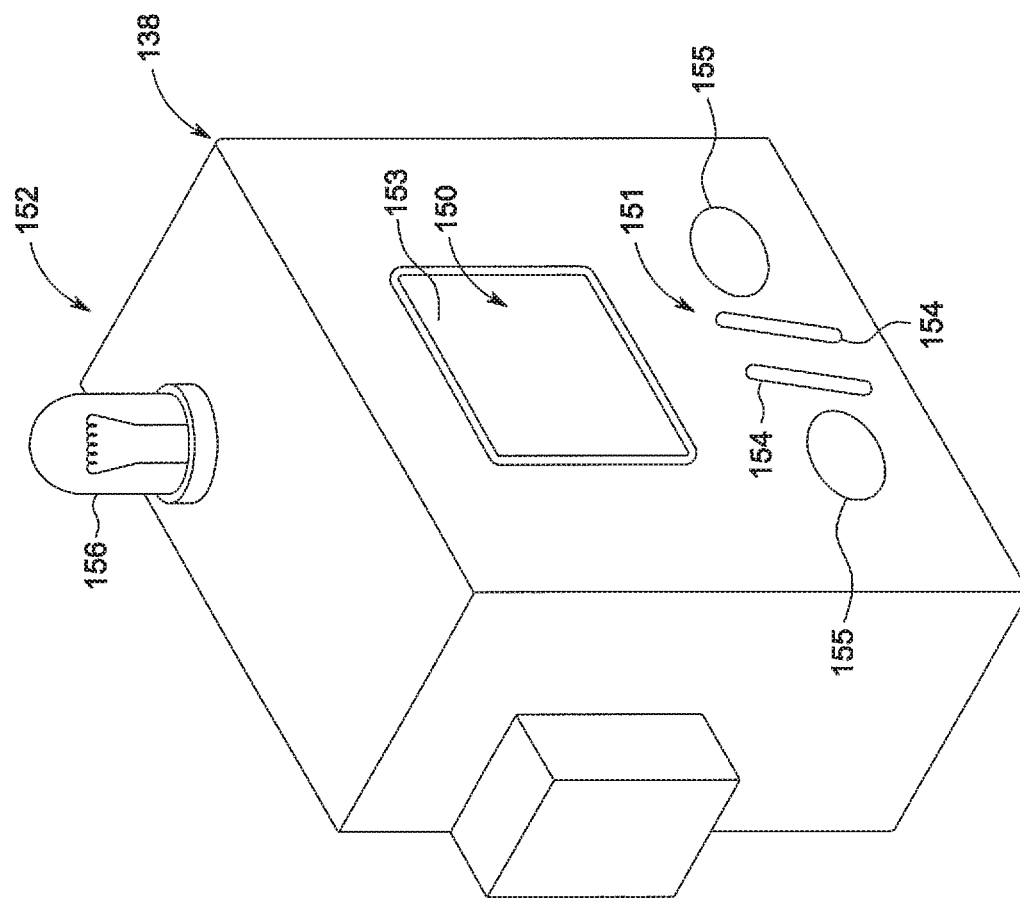
FIG. 16 illustrates a control panel according to various embodiments.

As introduced above, the control system 100 may include a control panel 138 for interfacing with the controller 103 and monitoring program 140 of the controller 103 via the interface unit 122. FIG. 16 illustrates one configuration of a control panel 138. The control panel 138 includes a graphical user interface 150 for displaying information related to the operation of the plant operations system 102 or control system 100. The control panel also comprises various peripherals such as selection devices 151 and indicators 152. As shown, the selection devices 151 include a touch screen 153, switches 154, and buttons 155. Other selections devices 151 may also be used, e.g., mouse, pointer, keyboard. One or more of the switches 154 or buttons 155 may comprise a hard button or soft button that may be selectively programmed according to user preference. The selection devices 151 may be configured to allow users to interface with the operations of the monitoring program 140 of the controller 103 to view, define, or modify operation conditions or set points. The selection devices 151 may also be configured to allow users to manually instruct the controller 103 to perform a control operation or override a control operation.

The indicator 152 may generally include media or mass communication device. As shown, the indicator 152 comprises light 156, however, additional or different devices such as speakers and, in some instances, text displays may be additionally or alternately used. The light 156 may be activated during specified operations of the operational system or may be used to indicate an operational condition, the occurrence of a trigger event, a warning, a pending notification, or for another reason defined in the monitoring program 120 or a control panel application. The indicator 152 may be programmed for multiple indication tasks defined by various operational states, e.g., multiple flashing sequences, to provide indicator capabilities for multiple situations. It is to be appreciated that the indicator 152 may be optional or may be located separate from the control panel 138. Indeed, in some embodiments, multiple indicators 152 may be located throughout the plant to provide notifications to users. The particular indicator 152 and manner or indication may be customized by the user. The user may also customize the notifications to identify one or more particular events or conditions as well as degrees of such events or conditions.

The control panel 138 may include a wired or wireless data or communication port 157 into which a user may couple a local or remote user access device 142 such as a computer, tablet, notebook, smart phone, mobile communication device, programming card, flash drive, memory stick, or special purpose diagnostic, programming, or system administration device. For example, in one embodiment, the control panel 138 includes a data port configured to receive a data storage device such as a flash drive defining one or more set points, administrative parameters, or security definitions. In some embodiments, the communication port 157 of the control panel 138 provides an access point to user access devices 142 to access the monitoring program 120 and its functionalities.

The control panel 138 may be located locally with respect to the plant operations system 102, e.g., on the line or production floor. The control panel 138 may provide users with a local access point to the control system 100. In one configuration, the control panel 138 includes a processor, memory, and communication port. The memory may store a control panel application configured to be executed by the processor and interface the user with the monitoring program 120. In various embodiments, the control panel 138 integrates with the processing, data storage, and communication functionalities of the controller 103 and monitoring program 120. The control panel 138 may be integrated with or in addition to a plant computer. In various configurations, users may use the control panel 138 to update or modify set points, initiate adjustments via the adjustment module 128, query the operations database 104 or analysis module 126 for operation data or analysis, e.g., to generate or define reports, view event logs, historical or projected performance, or real-time operation data or operational conditions, which may include interfacing with the sensor module 124 to initiate collection of real-time operation data. The control panel 138 may also allow users to access, define, or modify security features such as permissions or user access levels, perform administrative tasks, override automated operations, or initiate, terminate, or modify operations.

Figure 17:
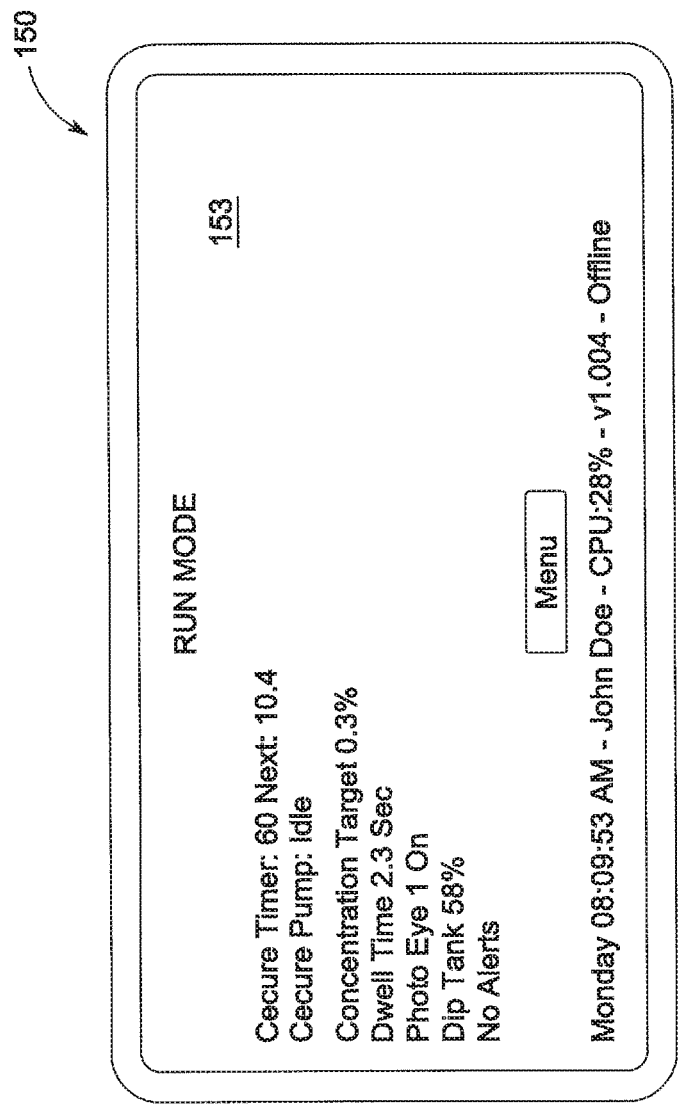
FIG. 17 illustrates a graphical user interface according to various embodiments.

FIG. 17 is a screen shot of the graphical user interface 150 according to various embodiments. The graphical user interface 150 includes identification of a mode of operation and specifies that the current mode is RUN or in operation. The graphical user interface 150 also identifies the time until the next scheduled addition of antimicrobial component and the state of the pump positioned to add the antimicrobial component. The graphical user interface 150 also identifies the target concentration and dwell time of the work pieces within the dip tank, the state of a photo eye sensor configured to detect work pieces, and the volume level of antimicrobial treatment solution within the dip tank. The graphical user interface 150 also provides an alert status, which is shown as no alerts pending. As described above, the graphical user interface 150 may include a touch screen interface. As shown, the graphical user interface 150 includes a menu selection wherein a user may touch the screen to pull up a control panel menu.

Figure 18:
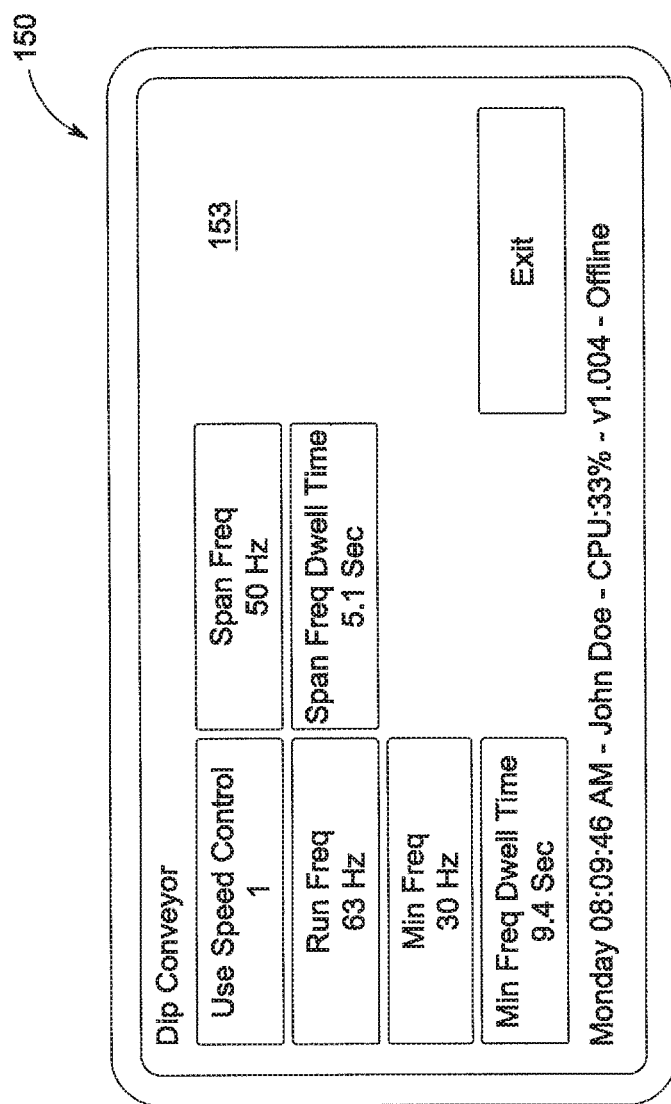
FIG. 18 illustrates a graphical user interface according to various embodiments.

FIG. 18 is another screen shot of the graphical user interface 150 showing a menu screen for use with a dip tank application identifying set points and their administrative states, as detected by the sensor module 124 and analyzed by the analysis module 126, corresponding to rows 57-62 of the set point table 130 of FIGS. 14A & 14B and identified by the English captions provided in column 135. Thus, a user may use the control panel 138 to view the current state of multiple aspects of the plant operations system 102 in real-time. In one embodiment, the user may select one of the identified set points to view or change the values defining the current set points. Typically, it will be preferable to require the user to establish authorization, e.g., by providing an identification or authorization code, before allowing the user to modify certain or any set point definitions or values.

As introduced above, the interface unit 122 may interface with notification devices 144 or access devices 142, which may include notification devices 144. Access devices 142, for example, may be configured to interact with the monitoring program 120 via access applications. Access applications may include one or more services though which access devices 142 or users of access devices 142 may interact with or utilize the monitoring program 120 functionalities. Access applications may be stored in-whole or in-part in data storage mediums associated with one or more access devices 142, the controller 103, the operations database 104, a control system 100 network, cloud, or other accessible location. Access applications may be configured to be executed by processors operatively associated with control system devices such as access devices 142, the controller 103, or operations database 104, e.g., an access application may be executed in-part by a remote processor for simulation on an access device 142. Access applications may include browsers configured to interact with one or more monitoring program 120 access applications or services, which may be bundled and purposed for the user according to the user's access level.

In various embodiments, the monitoring program 120 includes a plurality of user access levels to ensure security and integrity of the control system 100. User access levels may be used to control access to the controller 103, monitoring program 120, and associated functionalities. Access levels may be associated with monitoring program 120 services or functionalities available to access devices 142 or users. For example, the monitoring program 120 may include ten access levels comprising various combinations of permissions to view, access, or modify operations of the plant operations system 102, e.g., read or edit current set point settings or detected states, override automation parameters or functions, initiate system responses to trigger events or bring particular systems on or offline. The combination of permissions granted to each access level may be limited by user authorization or access device 142 and therefore may provide different functionalities for different users or access devices 142. Access applications may be configured to present user profiles, security credentials, or certificates that define the level of access and monitoring program 120 functionalities available to a user, e.g., actions or information available to a user using the application. Access levels may vary by location of the access device, manner of interface, e.g., type of device, connection protocol, network path, format, or identity of the user. In one configuration, the interface unit 122 is configured to verify users, e.g., verification of credentials, permissions, or clearances of users as defined in the monitoring program 120. Users may be required to provide identifying data such as a password, device information, or location.

In various embodiments, access applications may include monitoring program 120 services comprising one or more administrative functionalities. Administrative functionalities may be configured to provide access to one or more controllers 103 or operations databases 104. Various levels of administrative functionalities may include defining or modifying set points, setting permissions, security levels, specifying notification or alert criteria, identifying applicable users or devices to be notified or alerted, manner of providing notifications such as text message, email or alarm.

In some embodiments, access applications may include monitoring program 120 services comprising one or more operation control functionalities configured for modifying the operation of the plant operations system 102. Various levels of operation control functionalities may include initiating, terminating, or modifying operations of the operations system 102 such as opening or closing valves and powering pumps on and off, and overriding administrative parameters or control operation instructions.

In certain embodiments, access applications may include monitoring program 120 services comprising one or more monitoring functionalities configured for monitoring the operations of the operations system 102 of one or more plants and may include access to one or more controllers 103 or operations databases 104. Various levels of monitoring functionalities may include access to the operations database 104 to view archived operation data, event logs, or performance and viewing real-time operation data or current states. The interface unit 122 may also be configured to transmit requested data, responses, confirmations, or data related to monitoring functions. Periodic, continuous, scheduled, or conditional data transmissions may be specified for transmission to access devices 142. The type and timing of the data transmissions may be defined by the user in accordance with the monitoring functionalities provided by the access application or may be defined at another access device 142, plant computer, or control panel 138. Monitoring functionalities may include transmissions of operation data or operational analysis. Monitoring functionalities may also include receiving transmissions of updates, notifications, such as alerts or alarms at an access device 142. For example, the analysis module 126 may be configured to identify various operational conditions, e.g., by performing operational condition analyses of operation data, and the interface unit 122 may be configured to transmit a notification such as an alert or alarm to specified access devices 142 or notification devices 144 associated with a user or group of users, e.g., using messaging services, text messages, prerecorded messages, pages, email. The notification may identify a type or level of alert, an administrative state or trigger event prompting the notification, a potential cause, etc. In one embodiment, the notification may identify a proposed solution. The proposed solution may be predefined to allow a user to quickly address the event. In one embodiment, for example, the notification provides one or more "one click" solution buttons that may be selected by the user to initiate a predefined response such as transmission of a control instruction to the adjustment module to initiate control operation to modify operation of the operations system 102, such as the antimicrobial application system 110. The notification may include a recent operation activity log relevant to the event or identify other users or access devices 142 receiving the notification or steps taken by such uses or access devices 142 to address the subject matter of the notification. The notification may also include a communication link to transmit messages or additional notifications to other users or access devices 142.

Access applications may also include one or more corporate functionalities. Corporate functionalities may be configured for use by corporate users and thus provide one or more levels of monitoring functionalities. The monitoring functionalities for corporate users may be modified to provide a broader overview of plant performance and may include the ability to generate or specify plant performance reports. In one embodiment, the corporate functionalities include access to plant performance reports from multiple plants, for example, via access to multiple operations databases 104, or to performance analyses from multiple plants compiled by the analysis module 126.

Figure 19:
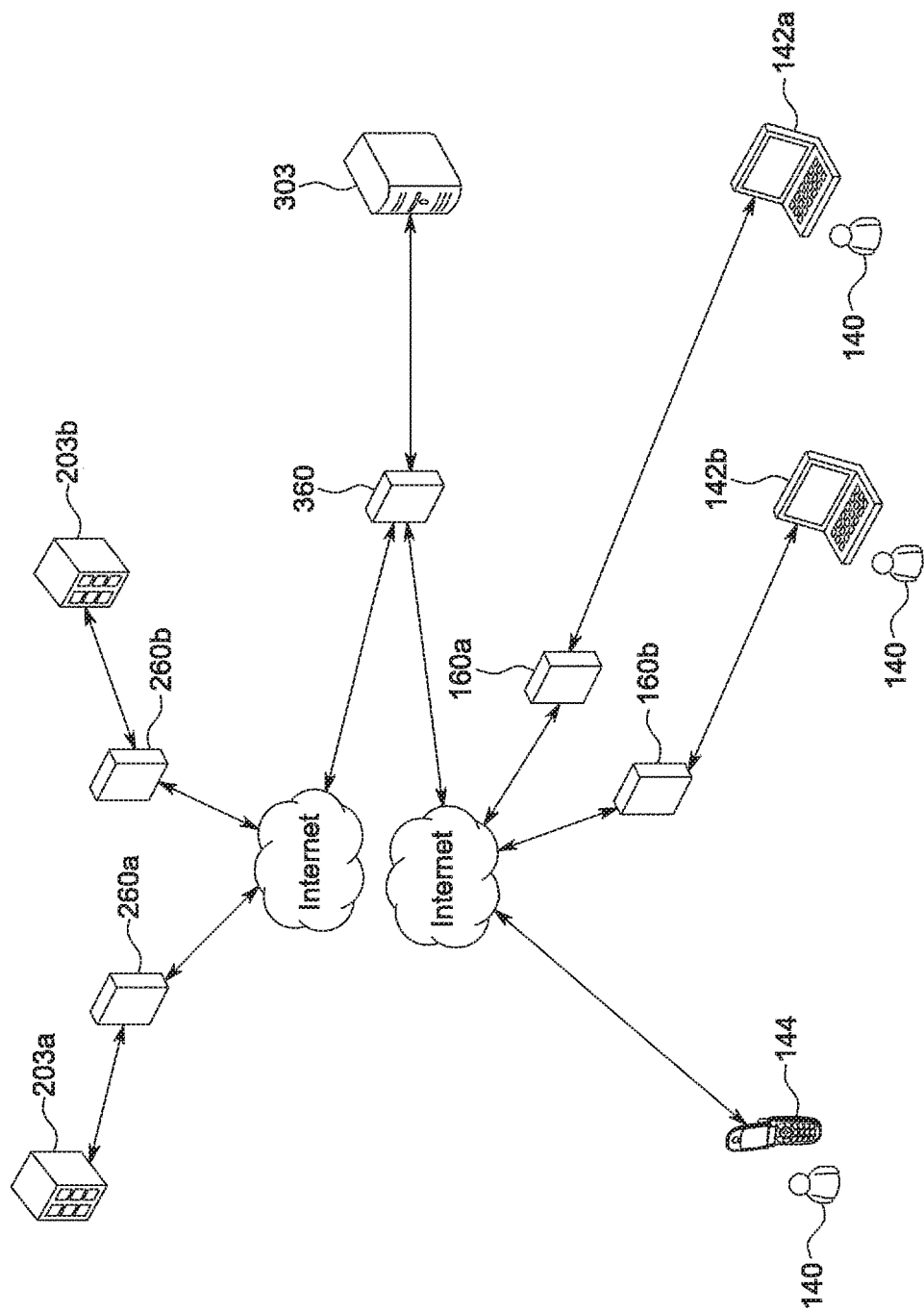
FIG. 19 schematically illustrates a control system comprising a multi-plant controller configured for real-time data routing and data storage according to various embodiments.
Figure 20:
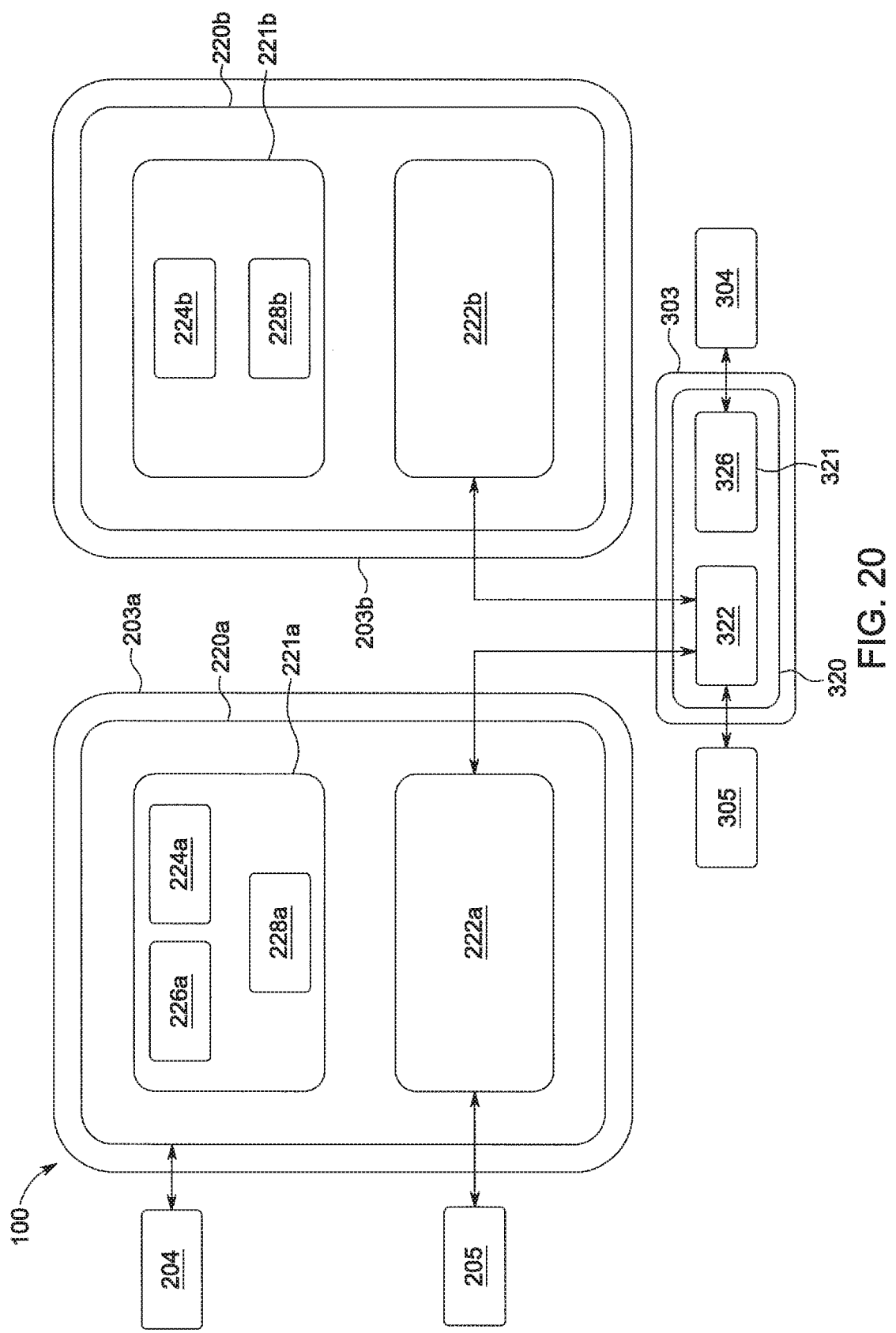
FIG. 20 schematically illustrates a control system comprising a multi-plant controller configured for real-time data routing and data storage according to various embodiments.

FIGS. 19 and 20 schematically illustrate two embodiments of the control system 100 in which the system 100 is configured for centralized monitoring and control of operations systems comprising an antimicrobial application system and associated units (not shown, see, e.g., FIG. 13). The control system 100 may be similar to the control system 100 described above where like features are similarly identified. Thus, the monitoring program 120 may comprise a plant monitoring program 220a, 220b and a multi-plant monitoring program 320 that may independently include or share the functionalities described above with respect to the monitoring program 120.

Each plant may comprise a plant controller 203a, 203b configured to collect operation data associated with the antimicrobial application system, e.g., an antimicrobial application unit, and is operable to control operations of the plant operations system. The multi-plant controller 303 may comprise a server such as a communication server and may be configured for real-time data routing and database storage. The first plant controller 203a and the second plant controller 203b are configured to transmit operation data to the multi-plant controller 303. The operation data may include real-time data. In one embodiment, each plant controller 203a, 203b is configured to transmit real-time operation data to the multi-plant controller 303 at scheduled intervals, such as every second or other specified time, upon request, or upon the occurrence of a trigger event. As described above, using access devices 142, set points may be remotely modified over an internet connection. The control system 100 may therefore include a distributed network architecture having a centralized server comprising the multi-plant controller into which the plant controllers 203a, 203b and access devices 142 remotely connect to interface with the operations of the antimicrobial application system.

The multi-plant monitoring program 320 and plant monitoring programs 220a, 220b may be configured to coordinate operations, communications, and various administrative tasks. Users may customize settings and the functionalities accessible via interfacing access devices 142 and notification devices 144 to suit the user's desired application. Operation data transmission may be wired or wireless depending on the application. As shown, the operation data is transmitted from each controller 203a, 203b to the multi-plant controller 303 over a distributed network. The transmissions may be transmitted through the fire wall/router 260a, 260b, 360a of each plant and the multi-plant controller 303, as shown in FIG. 19. For example, the data may be transmitted using an internet or telecommunications connection.

The multi-plant controller 303 may include or maintain a multi-plant operations database 304, which may or may not include, in whole or in part, individual plant operations databases 204. The multi-plant operations database 304 may archive, log, or maintain operation data and related analysis, store generated statistics or reports, or provide access to individual or multi-plant statistics. The multi-plant operations database 304 may also provide access to historical operation data, analysis, event logs, etc. or provide such information for generation of single or multi-plant reports.

Referring to FIG. 19, the notification device 144 and access devices 142a, 142b may be in one or two-way communication with the multi-plant controller 303, which may include communications transmitted between firewalls/routers 160a, 160b, 260. Notably, with respect to the plant operations system, the access devices 142a, 142b or notification devices 144 are not limited by a local or remote location. For example, a user may access the multi-plant monitoring program 320 (see FIG. 20) at an access device 142a, 142b or receive notifications at a notification device 144 whether the user or device 142a, 142b, 144 is on the plant floor or offsite. Thus, the multi-plant controller 303 may be configured as a central point from which data may be routed and operations may be controlled.

Access device 142*a* may be configured for use by a service technician user 140*a*. Depending on the access level of the access device 142*a* or user 140*a*, access device 142*a* may include or have access to one or more access application services having monitoring, operation control, or administrative functionalities as described above. For example, the user 140*a* of access device 142*a* may perform or define plant monitoring operations, set, define, or receive notifications such as real-time notifications, alerts, or alarms, define user access levels or perform other user administration tasks, or otherwise set or modify system settings. For example, an engineer located remotely may be provided with access to one or more plants, which may be located anywhere in the world. Using the control system 100 the engineer may remotely change and adjust the operation of the antimicrobial application system. Thus, the engineer may obtain real-time operation data and modulate operation and administrative parameters in real-time.

Access device 142*b* may be configured for use by a corporate user 140*b*. Depending on the access level of the access device 142*b* or user 140*b*, access device 142*b* may include or have access to one or more monitoring functionalities as described above. For example, the user 140*b* of access device 142*b* may view or receive plant performance history or define performance report criteria or frequency with respect to one or multiple plants.

Notification device 144 may be configured for use by a notification user 140*c* to receive notifications as defined in the monitoring program 220*a*, 220*b* of one or both plants or the multi-plant monitoring program 320, which may include a dedicated plant monitoring program for each plant. Notifications may include alarms, text messages, emails, etc., as described above. Notifications received at notification devices 144 configured for two-way communication may allow the user to respond to the notification or transmit a confirmation to the multi-plant controller 320 of receipt or read of the notification.

The multi-plant monitoring program 320 may be configured to handle control system data, e.g., route, store, or process operations data, analyze operational conditions, generate reports, event logs, notifications, etc. The multi-plant monitoring program 320 may include, replace, integrate, or be configured to interface with the plant monitoring program 220*a*, 220*b*. The multi-plant administration program 320 may be configured to provide remote monitoring and control functionalities, some of which may overlap or be in addition to those of the plant monitoring program 220*a*, 220*b*. In one embodiment, the plant monitoring program 220*a*, 220*b* provides local control and monitoring functions, e.g., using a control panel, which may be similar to control panel 138 described above.

The plant controller 203*a* may submit control instructions received from the multi-plant controller 303, which may be in addition to or different from control instructions provided by the analysis module 226*a*. In at least one embodiment, the plant controller 203*a* may be selectively configurable to operate as a slave controller and the multi-plant controller 303 is selectively configurable to operate as the master controller to direct or override the operation of the plant controller 203*a*.

In various embodiments, the multi-plant controller 303 may function as a central monitoring or control service for multiple plants, an intermediate service for remote monitoring or control of individual plants, a plant oversight service, or a plant startup or auditing service, for example. It is to be appreciated that the level of service provided by the multi-plant controller 303 to each plant may not be the same. For example, the multi-plant controller 303 may provide monitoring service for a first plant and monitoring and control service for a second plant.

As introduced above, the plant monitoring program 220*a*, 220*b* and the multi-plant monitoring program 320 may independently include or share functionalities. Referring to FIG. 20, the plant controller 203*a*, 203*b* includes a monitoring program 220*a*, 220*b*, which may be similar to the monitoring program 120 described above with respect to FIG. 13, and an operations unit 221*a*, 221*b*. The operations unit comprises a sensor module 224*a*, 224*b* operatively coupled to a plurality of sensors to receive operation data. The monitoring program 220*a* of the plant controller 203*a* may also include an analysis module 226*a* to analyze operation data according to the monitoring program 220*a*. The multi-plant controller 303 includes a multi-plant monitoring program 320 comprising an operation unit 321 and an interface unit 322. In this configuration, the interface unit 222*a*, 222*b* of the plant monitoring program 220*a*, 220*b* transmits operation data, notifications, states, trigger events, event logs, or other data to the interface unit 322 of the multi-plant program 320. The multiple-plant controller 303 may analyze the data using a multi-plant analysis module 326 to determine if operational conditions are within set points. As described above, the set points may be static or dynamic. Thus, the multi-plant controller 303 may perform an initial or second data analysis, as the case may be. In other embodiments, the analysis of the operation data is distributed between the plant monitoring program 220*a*, 220*b* and the multi-plant monitoring program 320, e.g., based on available resources or as otherwise desired. The multi-plant controller 303 and monitoring program 320 may provide oversight functions for the control system 100 with respect to one or more plant controllers 203*a*, 203*b* or operation thereof. The multi-plant analysis module 326 of the multi-plant controller 303 may also perform data analysis functions for the plant controller 203*b*. The multi-plant interface unit 322 may also transmit notifications and provide access to interfaces 305 which may be in addition to or instead of transmission of notifications or access provided to interfaces 222*a*, 222*b* by the plant interface unit 222*a*.

Plant controller 203*b* includes monitoring program 220*b* configured with an interface unit 222*b* and an operations unit 221*b*. The operations unit comprises a sensor module 224*b*, and an adjustment module 228*b*. The interface unit 222*b* is configured to transmit operation data obtained by the sensor module 224*b* to the multi-plant interface unit 322 for analysis by the multi-plant analysis module 326. The multi-plant analysis module 326 may be configured to analyze the operation data and respond using administrative decision rules similar to that described above with respect to analysis module 126. The multi-plant analysis module 326 may be configured to generate reports or files, update previously generated reports or files, and store or distribute the reports, files, or updated reports or files. The multi-plant analysis module 326 may be configured to provide analysis, reports, and notifications, e.g., alerts or warnings, to interfaces 305 such as access or notification devices 142, 144, via the interface unit 322. The multi-plant interface module 322 may also be configured to route to the adjustment module 228*b*, or in some embodiments to the adjustment module 228*a*, control operation instructions received from authorized users or access devices 142 or from the multi-plant analysis module 326 in response to a trigger event, e.g., as defined by administrative decision rules.

The foregoing description of various embodiments of the present invention is provided to enable any person skilled in the art to make and use the present invention and its embodiments. Various modifications to these embodiments are possible, and the generic principles presented herein may be applied to other embodiments as well.

It will be apparent to one of ordinary skill in the art that some of the embodiments as described hereinabove may be implemented in many different embodiments of software, firmware, and hardware in the entities illustrated in the figures. The actual software code or specialized control hardware used to implement some of the present embodiments do not limit the present invention.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for receiving, storing and/or processing data for standalone application and/or over a networked medium or media. For example, various embodiments may include access devices or be configured to communicate, e.g., transmit data or interface, with the control system and program as described herein.

Computers and computer systems described herein may include operatively associated computer-readable memory media such as memory for storing software applications and instructions used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, DVD, compact disc, memory stick, ROM (read only memory), RAM (random access memory), PROM (programmable ROM), EEPROM (extended erasable PROM), and/or other like computer-readable media.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, Compact Disk Read Only Memory (CD-ROM), Compact Disk Recordable (CD-R), Compact Disk Rewriteable (CD-RW), optical disk, magnetic media, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth. The embodiments are not limited in this context.

It can be appreciated that, in certain aspects, a single component may be replaced by multiple components, and multiple components may be replaced by a single component, to provide an element or structure or to perform a given function or functions. Except where such substitution would not be operative to practice certain embodiments of the present invention, such substitution is considered within the scope of the present invention.

The control system and operations system, which may include an antimicrobial application system, has been illustrated and described as comprising several separate functional elements, such as modules or units. Although certain of such modules or units may be described by way of example, it can be appreciated that a greater or lesser number of modules or units may be used and still fall within the scope of the embodiments. Further, although various embodiments may be described in terms of modules or units to facilitate description, such modules or units may be implemented by one or more hardware components (e.g., processors, DSPs, PLDs, ASICs, circuits, registers, servers, clients, network switches and routers), software components (e.g., programs, subroutines, logic) and/or combination thereof.

In various embodiments, the control system or application system, including antimicrobial application equipment, may comprise multiple modules connected by one or more communications media. Communications media generally may comprise any medium capable of carrying information signals. For example, communications media may comprise wired communications media, wireless communications media, or a combination of both, as desired for a given implementation. Examples of wired communications media may include a wire, cable, printed circuit board (PCB), backplane, semiconductor material, twisted-pair wire, coaxial cable, fiber optics, and so forth. An example of a wireless communications media may include portions of a wireless spectrum, such as the radio-frequency (RF) spectrum. The embodiments are not limited in this context.

The modules or units may comprise, or be implemented as, one or more systems, sub-systems, devices, components, circuits, logic, programs, or any combination thereof, as desired for a given set of design or performance constraints. For example, the modules may comprise electronic elements fabricated on a substrate. In various implementations, the electronic elements may be fabricated using silicon-based IC processes such as complementary metal oxide semiconductor (CMOS), bipolar, and bipolar CMOS (BiCMOS) processes, for example. The embodiments are not limited in this context Unless specifically stated otherwise, it may be appreciated that terms such as "processing", "generating", "calculating", "determining", "analyzing" or the like, refer to the action or processes of a computer or computing system, or similar electronic computing device, that manipulates or transforms data represented as physical quantities (e.g., electronic) within the computing system's registers or memories into other data similarly represented as physical quantities within the computing system's memories, registers or other such information storage, transmission or display devices. The embodiments are not limited in this context. An action such as "identifying" when performed by a computer or computer system may include identification by determining, accessing system data, comparisons with system data, instructions, or the like. An action such as initiating may include causing an event or thing initiated either directly or indirectly. For example, initiating may include signaling, providing power or instructions, physical manipulation, transmission of data, calculation of conditions, or other step resulting in the event sought to be initiated. Furthermore, an action such as "storing", when used in reference to a computer or computer system, refers to any suitable type of storing operation including, for example, storing a value to memory, storing a value to cache memory, storing a value to a processor register, and/or storing a value to a non-volatile data storage device. Various embodiments are described and illustrated in this specification to provide an overall understanding of the composition, function, operation, and application of the disclosed system, apparatus and methods. It is understood that the various embodiments described and illustrated in this specification are non-limiting and non-exhaustive. Thus, the invention is not necessarily limited by the description of the various non-limiting and non-exhaustive embodiments disclosed in this specification. The features and characteristics illustrated or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further, Applicant reserves the right to amend the claims to affirmatively disclaim features or characteristics that may be present in the prior art. Therefore, any such amendments comply with the requirements of 35 U.S.C. §§ 112(a) and 132(a). The various embodiments disclosed and described in this specification can comprise, include, consist of, or consist essentially of the features and characteristics as variously described in this specification.

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference into this specification. Any material, or portion thereof, that is said to be incorporated by reference into this specification, but which conflicts with existing definitions, statements, or other disclosure material set forth in this specification, is only incorporated to the extent that no conflict arises between that incorporated material and the existing disclosure material. Applicants reserve the right to amend this specification to expressly recite any subject matter, or portion thereof, incorporated by reference into this specification.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an implementation of the described embodiments. Further, the use of a singular noun includes the plural, and the use of a plural noun includes the singular, unless the context of the usage requires otherwise.

The matter set forth in the foregoing description and accompanying drawings is offered by way of illustration only and not as a limitation. While the systems, methods, compositions, and devices for recycling of antimicrobial treatment solution have been described and illustrated in connection with certain embodiments, many variations and modifications will be evident to those skilled in the art and may be made without departing from the spirit and scope of the disclosure. For example, the systems, methods, compositions, and devices disclosed herein have been identified, adapted to, and designed for food processing use, and particularly to processing of chicken and other poultry parts. Those having skill in the art will understand upon reading the present disclosure that the subject matter may be applied to other processing uses. The disclosure is thus not to be limited to the precise details of methodology or construction set forth above as such variations and modification are intended to be included within the scope of the disclosure.

What is claimed is:

1. A control system for monitoring antimicrobial treatment equipment of multiple antimicrobial application systems, the control system comprising:
   a multi-plant controller configured to execute a multi-plant monitoring program, the multi-plant monitoring program comprising:
      a multi-plant interface unit configured to receive real-time operation data from a plurality of antimicrobial application systems each comprising antimicrobial application equipment operatively coupled to the multi-plant controller and controllable by the multi-plant controller, and
      a multi-plant operations unit comprising a multi-plant analysis module configured to analyze the real-time operation data and initiate a specified response when the analysis indicates that a trigger event has occurred, wherein the response comprises at least one of issuing a notification to one or more notification devices or initiating a control operation at one or more antimicrobial application equipment to modify an operation thereof.

2. The control system of claim 1, wherein the multi-plant controller is configured to receive the real-time operation data over a distributed network from a local plant controller associated with each of the plurality of antimicrobial application systems.

3. The control system of claim 2, wherein multi-plant controller is further configured to transmit control operations to the local plant controller associated with each of the plurality of antimicrobial application systems to initiate the control operations.

4. The control system of claim 3, wherein the antimicrobial application equipment comprises one or more components of the group comprising:
   a rotary screen filter comprising a rotatable, cylindrical body defined by a screen and into which antimicrobial treatment solution is received for filtration of solid components,
   a plurality of spray nozzles positioned to direct antimicrobial treatment solution onto work pieces as the work pieces are conveyed through a spray cabinet,
   a dip tank for containing antimicrobial treatment solution and a conveyer for conveying work pieces through the antimicrobial treatment solution contained in the dip tank,
   a suction box configured to fluidically couple to a dip tank and including a sensor for sensing a level of antimicrobial treatment solution in the dip tank, a capture unit comprising a series of activated carbon filters to filter antimicrobial component from an antimicrobial treatment solution, and a capture unit comprising a series of activated carbon filters each including a header having a plurality of arms defining fluid ports for distributing antimicrobial treatment solution over the activated carbon.

5. The control system of claim 1, wherein the multi-plant interface unit is configured to provide a remote interface to authorized mobile access devices.

6. The control system of claim 5, wherein the remote interface is operable to allow authorized access devices to define or control operations of the multi-plant controller including at least one of initiating collection of real-time operation data from one or more of the plurality of antimicrobial application systems and initiating a control operation at one or more antimicrobial application equipment to modify an operation thereof using the multi-plant adjustment module.

7. The control system of claim 6, wherein the multi-plant interface unit comprises multiple access levels providing different functionalities to authorized access devices for each access level.

8. The control system of claim 7, wherein user mobile access device comprises one of a smart phone, tablet, or other mobile device having a display screen.

9. A method of monitoring an antimicrobial application equipment, the method comprising:
- collecting operation data from a plurality of sensors positioned to detect real-time operation data associated with operation of the antimicrobial application equipment;
- analyzing the operation data to determine an operational condition;
- comparing the operational condition to a set point to identify an administrative state corresponding to the set point;
- and applying an administrative decision rule to the administrative state and initiating a response specified by the decision rule when the administrative state corresponds to a trigger event;

wherein the antimicrobial application equipment comprises one or more components of the group comprising:
- a rotary screen filter comprising a rotatable, cylindrical body defined by a screen and into which antimicrobial treatment solution is received for filtration of solid components, wherein the operation data comprises flow rate through the rotary screen filter or the presence, number, orientation, or rate of work pieces,
- a plurality of spray nozzles positioned to direct antimicrobial treatment solution onto work pieces as the work pieces are conveyed through a spray cabinet, wherein the operation data comprises nozzle pressure or the presence, number, orientation, or rate of work pieces,
- a dip tank for containing antimicrobial treatment solution and a conveyer for conveying work pieces through the antimicrobial treatment solution contained in the dip tank, wherein the operation data comprises depth or volume of antimicrobial solution in the dip tank or the presence, number, orientation, or rate of work pieces,
- a suction box configured to fluidically couple to a dip tank and including a sensor for sensing a level of antimicrobial treatment solution in the dip tank, wherein the operation data comprises depth or volume of antimicrobial solution in the dip tank or the presence, number, orientation, or rate of work pieces,
- a first capture unit comprising a first series of activated carbon filters to filter antimicrobial component from an antimicrobial treatment solution, wherein the operation data comprises flow rate through the first series of activated carbon filters or the presence, number, orientation, or rate of work pieces, and
- a second capture unit comprising a second series of activated carbon filters each including a header having a plurality of arms defining fluid ports for distributing antimicrobial treatment solution over the activated carbon, wherein the operation data comprises flow rate through the second series of activated carbon filters or the presence, number, orientation, or rate of work pieces.

* * * * *